United States Patent [19]

Van Daele

[11] Patent Number: 4,766,125
[45] Date of Patent: Aug. 23, 1988

[54] N-ARYL-PIPERAZINEALKANAMIDES USEFUL FOR PROTECTING HEARTS FROM MYOCARDIAL INJURY CAUSED BY ISCHAEMIA, ANOXIA OR HYPOXIA

[75] Inventor: Georges Van Daele, Turnhout, Belgium

[73] Assignee: Janssen Pharmaceutica N.V., Beerse, Belgium

[21] Appl. No.: 362,814

[22] Filed: Mar. 29, 1982

Related U.S. Application Data

[63] Continuation-in-part of Ser. No. 276,624, Jun. 23, 1981, abandoned.

[51] Int. Cl.$^4$ .................. A61K 31/495; C07D 295/10
[52] U.S. Cl. ..................................... 514/255; 544/399
[58] Field of Search ............... 544/399, 396, 397, 398; 424/50; 514/255

[56] References Cited

U.S. PATENT DOCUMENTS

| | | | |
|---|---|---|---|
| 2,997,473 | 8/1961 | deJongh et al. | 544/396 |
| 3,267,104 | 8/1966 | Karel | 544/399 |
| 3,654,277 | 4/1972 | Winter | 544/399 |
| 3,681,359 | 8/1972 | Leigh et al. | 544/399 |
| 3,953,884 | 4/1976 | Podesva et al. | 544/397 |
| 4,079,137 | 3/1978 | Cyrus et al. | 544/396 |

FOREIGN PATENT DOCUMENTS

| | | | |
|---|---|---|---|
| 741358 | 4/1970 | Belgium | 544/392 |
| 1577338 | 3/1968 | France | 544/392 |
| 276807 | 4/1962 | Netherlands | 544/397 |
| 1196721 | 7/1970 | United Kingdom | 544/398 |

OTHER PUBLICATIONS

Janssen Pharmaceutica "1,4 Disubstituted Piperazines and Diazepines," Chem. Abst. 64: 12704(g) (1966).
Borgers et al., "Shifts of Calcium in the Ischemic Myocardium," Chem. Abst. 99: 20494m (1982).
Royal Society of Medicine International Congress and Symposium Series, No. 29, pp. 89-95 (1980).
Helv. Chim. Acta, 45, 2383-2402 (1962).
Chemical Abstracts 90, 168,547.
The Journal of Pharmacology and Experimental Therapeutics, 152(2), 265-274 (1966).
Langer, G. A., "The Structure and Function of the Myocardial Cell Surface", (1978) Am. J. Physiol., 235, H461.
Lullman, H. and Peters, T. (1977), "Plasmalemmal Calcium in Cardiac Excitation-Contraction Coupling," Clin. Exp. Pharmacol. Physiol., 4, 49.
Fabiato, A., and Fabiato, F., "Calcium Release from the Sarcoplasmic Reticulum," (1977), Circ. Res., 40, 119.
Fabiato, A., and Fabiato F., "Calcium-Induced Release of Calcium from the Sarcoplasmic Reticulum of Skinned Cells from Adult Human, Dog, Cat, Rabbit, Rat, and Frog Hearts and from Fetal and New-Born Rat Ventricles," (1978), Ann. N.Y. Acad. Sci., 307, 491.
Chiesi, M., Ho, M. M., Inesti, G., Somlyo, A. V. and Somlyo, A. P., "Primary Role of Sarcoplasmic RCticulum in Phasic Contractile Activation of Cardiac Myocytes with Shunted Myolemma," (1981) J. Cell Biol., 91, 728.
Diculescu, I., Popepscu, L. M., Ionescu, N. and Butucescu, N. "Ultrastructural Study of Calcium Distribution in Cardiac Muscle Cells,", (1971) Z. Zellforsch., 121,181.
Flameng, W., Daenen W., Borgers, M., Thone, F., Xhonneux, R., Van de Water, A. and Van Belle, H. (1981) Circulation, 64, 796.
Borgers, M., Flameng, W., Daenen, W., Xhonneux, R. and Thone, F., "The Role of Calcium in Ischemic Damage to Heart Muscle," (1981), Bibl. Anat., 30, 507.
Legato, M. J. and Langer, G. A., "The Subcellular Localization of Calcium Ion in Mammalian Myocardium," (1969) J. Cell. Biol., 41, 401.
Bianchi, C. P., "Pharmacology of Excitation-Contraction Coupling in Muscle," (1969) Fed. Proc., 28, 1624.
Borgers, M., De Brabander, M., Van Reempts, J., Awouters, R. and Jacob W. "Intranuclear Microtubules in Lung Mast Cells of Guinea Pigs in Anaphylactic Shock," (1977), Lab. Invest., 37, 1.
Borgers, M., "Factors Influencing the Course of Myocardial Ischemia", Debakey and Gotto (eds.) Elsevier Sci. Publ. B.V. (1983) in Chap. 4, p. 55.
Somlyo, A. V., Gonzalez-Serratos, H., Shuman, H., McAllan, G. and Somlyo, A. P., "Calcium Release and Ionic Changes in the Sarcoplasmic Reticulum of Tetanized Mucle: An Electron-Probe Study," (1981), J. Cell Biol., 90, 577.
Borgers, M., Thone, F. and Van Neuten, J. M. "The Subcellular Distribution of Calcium and the Effects of Calcium-Antagonists as Evaluated with a Combined Oxalate-Pyroantimonate Technique," (1981), Acta. Histochem., 24, 327.
Wohlfart, B. and Nobel, M. I. M., "The Cardiac Excitation-Contraction Cycle," (1982), Pharmacol. Ther. vol. 16, pp. 1-43.
Hendrickson, H. S. and Fullington, J. G. "Stabilities of Metal Complexes of Phospholipids: Ca(II), Mg(II), and Ni(II) Complexes of Phosphatidylserine and Triphosphoinositide," (1965), vol. 4, No. 8, p. 1599.
Dawson, R. M. C. "Phosphatido-Peptide'-Like Complexes Formed by the Interaction of Calcium Triphosphoinositide with Protein", (1965), Biochem. J., vol. 97, p. 134.
Philipson, K. D., Bers, D. M. and Nishimoto, A. Y. "The Role of Phospholipids in the $Ca^{2+}$ Binding of Isolated Cardiac Sarcolemma", (1980), J. Mole. Cell. Cardiol, vol. 12, p. 1159.
Langer, G. A., Frank, J. S. and Philipson, K. D., "Ultrastructure and Calcium Exchange of the Sarcolemma, Sarcoplasmic Reticulum and Mitochondria of the Myocardium," (1982) Pharmacol. Ther., vol. 16, p. 331.

Primary Examiner—Donald G. Daus
Assistant Examiner—Cecilia Shen
Attorney, Agent, or Firm—Geoffrey G. Dellenbaugh

[57] ABSTRACT

Novel N-aryl-piperazinealkanamides, having particular substituents attached to one of the carbon atoms of the piperazine ring, which compounds are useful to protect hearts from myocardial injury caused by ischaemia, anoxia or hypoxia.

18 Claims, No Drawings

N-ARYL-PIPERAZINEALKANAMIDES USEFUL FOR PROTECTING HEARTS FROM MYOCARDIAL INJURY CAUSED BY ISCHAEMIA, ANOXIA OR HYPOXIA

CROSS-REFERENCE TO RELATED APPLICATIONS

This application is a continuation-in-part of our copending application Ser. No. 276,624, filed June 23, 1981 now abandoned.

BACKGROUND OF THE INVENTION

Piperazine derivatives, bearing on one of the carbon atoms a lower alkyloxycarbonyl radical or a hydroxymethyl radical, are described in Helv. Chim. Acta, 45, 2383–2402 (1962). These piperazine derivatives are taught to be useful as anthelmintics, antihistaminics and as psychotropic drugs.

N-aryl-4-(4,4-diarylbutyl)-1-piperazinealkanamides, which are optionally substituted on one of the piperazine carbon atoms with a methyl radical, are described in U.S. Pat. No. 3,267,104. Said piperazinealkanamides are taught to be useful as coronary vasodilators, as local anaesthetics, as central nervous system stimulating agents and as anticarriageenin agents.

N-aryl-piperazineacetamides which are optionally substituted in the piperazine part with a methyl or a phenyl radical, are described in C.A. 90, 168, 547 as useful intermediates in the preparation of analgesics.

The compounds of the present invention differ from the aforementioned prior art compounds by the nature of the substituents on the piperazine moiety and by their pharmacological properties.

DESCRIPTION OF THE PREFERRED EMBODIMENTS

The present invention is concerned with novel piperazine derivatives, which may be represented by the formula

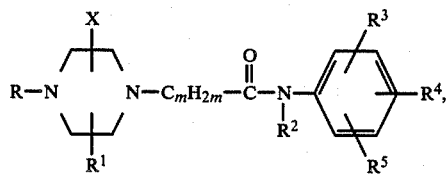

the stereochemically isomeric forms and the pharmaceutically acceptable acid addition salts thereof, wherein $R^1$ is a member selected from the group consisting of hydrogen and lower alkyl;

X is a member selected from the group consisting of hydroxylower alkyl, lower alkyloxylower alkyl, aminocarbonyl, mono- and di(lower alkyl)aminocarbonyl, carboxyl, lower alkyloxycarbonyl, (aminocarbonyl)lower alkyl, [mono- and di(lower alkyl)aminocarbonyl]lower alkyl, carboxylower alkyl, (lower alkyloxycarbonyl)lower alkyl and (hydroxylower alkyl)aminocarbonyl;

m is the integer 1 or 2;

$R^2$ is a member selected from the group consisting of hydrogen and lower alkyl;

$R^3$, $R^4$ and $R^5$ are each independently selected from the group consisting of hydrogen, hydroxy, lower alkyl, lower alkyloxy, halo, trifluoromethyl, lower alkylcarbonyl, aminocarbonyl, lower alkyloxycarbonyl, cyano, amino, mono- and di(lower alkyl)amino, (lower alkylcarbonyl)amino and (aminocarbonyl)amino, while $R^3$ and/or $R^4$ may also be nitro; and R is a member selected from the group consisting of a radical having the formula

wherein $Ar_1$ and $Ar_2$ are each an aryl radical; and a radical having the formula

wherein

Alk is an alkanediyl radical or a lower alkenediyl radical, said lower alkanediyl radical being optionally substituted by a hydroxy- or a lower alkyl radical; and Q is a member selected from the group consisting of aryl, aryloxy, diarylmethoxy, 2,2-diarylethenyl, diarylmethylcarbonyl, arylcarbonyl, mono- and diarylaminocarbonyl, diarylmethyl, the methyl moiety in said diarylmethyl group being optionally substituted with a cyano-, an aminocarbonyl-, a mono- or dilower alkylaminocarbonyl- or a lower alkyloxycarbonyl radical, arylamino, said amino moiety being optionally substituted with an aryl, arylcarbonyl-, a lower alkylcarbonyl-, an arylsulfonyl- or a lower alkylsulfonyl radical, 2,3-dihydro-2-oxo-1H-benximidazol-1-yl, being optionally substituted in the 5- or 6-position by halo, 10H-phenothiazin-10-ylcarbonyl, being optionally substituted by a halo atom, 1,2,3,6-tetrahydro-1,3-dimethyl-2,6-dioxo-7H-purin-7-yl, 1-aryl-1,3-dihydroisobenzofuran-1-yl, and 2,2-diaryl-1,3-dioxolan-4-yl;

wherein aryl is a member selected from the group consisting of phenyl, substituted phenyl, naphthalenyl, thienyl and pyridinyl, said substituted phenyl having from 1 to 2 substituents, each independently selected from the group consisting of halo and (halo-substituted phenyl)carbonyl.

In the foregoing definitions the term halo is generic to fluoro, chloro, bromo and iodo; the term "lower alkyl" is meant to include straigth and branched saturated hydrocarbon radicals having from 1 to 6 carbon atoms, such as, for example, methyl, ethyl, 1-methylethyl, 1,1-dimethylethyl, propyl, butyl, pentyl, hexyl and the like; "lower alkanediyl", as used in the definition of Alk, comprises straight and branched alkanediyl chains having from 1 to 6 carbon atoms; and "lower alkenediyl", as used in the definition of Alk, comprises straight and branched alkenediyl chains having from 2 to 6 carbon atoms.

Preferred compounds within the invention are those wherein R is a radical of formula (b) wherein Q is diarylmethyl and Alk is a 1,3-propanediyl radical.

Especially preferred compounds within the invention are those wherein R is a radical of formula (b), wherein Q is diarylmethyl and Alk is 1,3-propanediyl, X is aminocarbonyl, m is 1, and R¹ and R² are both hydrogen.

The most preferred compounds within the invention are selected from the group consisting of 3-(aminocarbonyl)-4-[4,4-bis(4-fluorophenyl)butyl]-N-(2,6-dichlorophenyl)-1-piperazineacetamide, the stereochemically isomeric forms and the pharmaceutically acceptable acid addition salts thereof.

The compounds of formula (I) can generally be prepared by the N-alkylation reaction of an appropriately substituted piperazine of formula (II) with a reagent of formula (III) or by the N-alkylation reaction of an appropriately substituted piperazine of formula (IV) with a reagent of formula (V).

of the reaction and, preferably, the reaction is carried out at the reflux temperature of the reaction mixture.

The compounds of formula (I) may also generally be prepared by reacting a piperazine of formula (II), respectively a piperazine of formula (IV), with the corresponding carbonyl-oxidated form of the reagent of formula (III), respectively (V), following art-known reductive amination procedures, i.e. by stirring and, if desired, heating the reactants together in a suitable reductive medium, e.g., under catalytic hydrogenation circumstances.

The compounds of formula (I) can also be prepared by stirring and heating an amide of formula (VI) with an appropriately substituted benzene derivative of formula

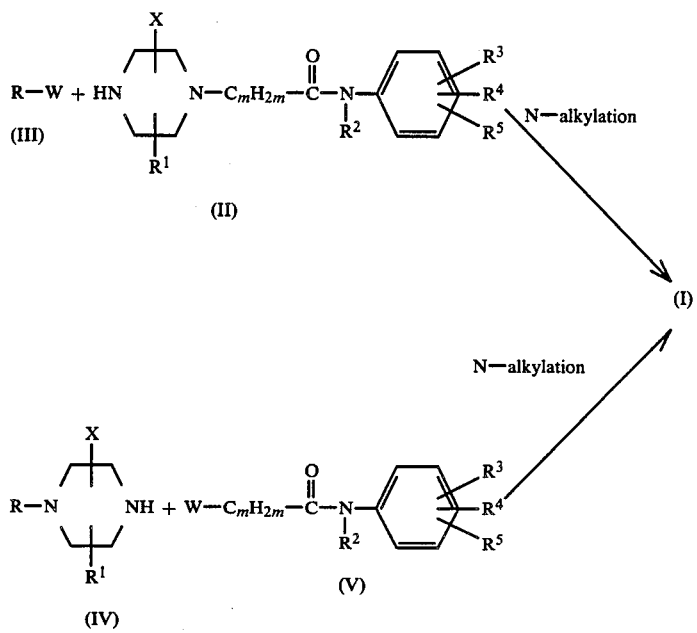

In the above reaction scheme R, R¹, R², R³, R⁴, R⁵, m and X are as previously described and W represents a reactive leaving group such as, for example, halo, e.g., chloro, bromo and iodo, or a sulfonyloxy group, e.g., methylsulfonyloxy, 4-methylphenylsulfonyloxy and the like.

The N-alkylation reaction of (II) with (III) and (IV) with (V) may generally be carried out in a suitable reaction-inert solvent such as, for example, a lower alkanol, e.g., methanol, ethanol, propanol, butanol and the like alkanols; an aromatic hydrocarbon, e.g., benzene, methylbenzene, dimethylbenzene, and the like; an ether, e.g., 1,4-dioxane, 1,1'-oxybispropane and the like; a ketone, e.g., 4-methyl-2-pentanone; N,N-dimethylformamide; nitrobenzene; and the like or a mixture of such solvents. The presence of an appropriate base such as, for example, an alkali or earth alkaline metal carbonate or hydrogen carbonate, e.g., potassium carbonate, sodium hydrogen carbonate and the like, an amine, e.g., N,N-diethylethanamine and the like, pyridine and the like, may be advantageous to pick up the acid which is liberated during the course of the reaction.

When W is other than an iodide radical, the presence of a small amount of an appropriate alkali or earth alkaline metal iodide, e.g., sodium iodide or potassium iodide, may act as a reaction promotor. Somewhat elevated temperatures are appropriate to enhance the rate (VII) in a suitable reaction-inert solvent, if desired, in the presence of an appropriate catalyst such as, for example, a cuprous chloride, boron trifluoride and the like.

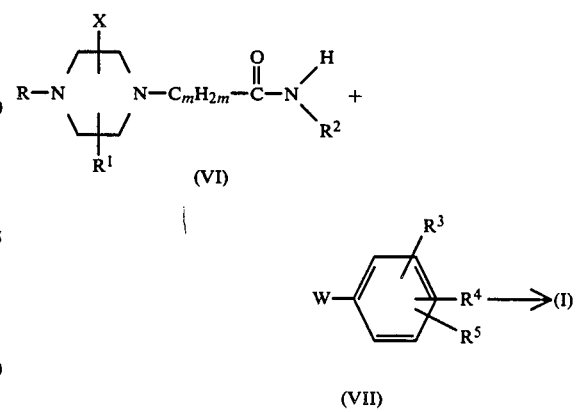

The compounds of formula (I) can also be prepared by the reaction of a carboxylic acid derivative of formula (VIII), wherein R⁶ is hydroxy, lower alkyloxy, aryloxy, amino, chloro, bromo or iodo, with an amine of formula (IX) by stirring and, if desired, heating the reactants together in a suitable solvent such as, for example, an alkanol, e.g., methanol, ethanol and the like; an ether, e.g., 1,4-dioxane, tetrahydrofuran and the like; N,N-dimethylformamide; 4-methyl-2-pentanone and the like.

formula (XII) with a reagent of formula (XIII) following the same procedure as a previously described for the reaction of (II) with (III).

In the following reaction-scheme the 1,2-ethanediyl radical in (X) or (XI) and in (XII) or (XIII) is substituted with a radical having the meaning of $R^1$.

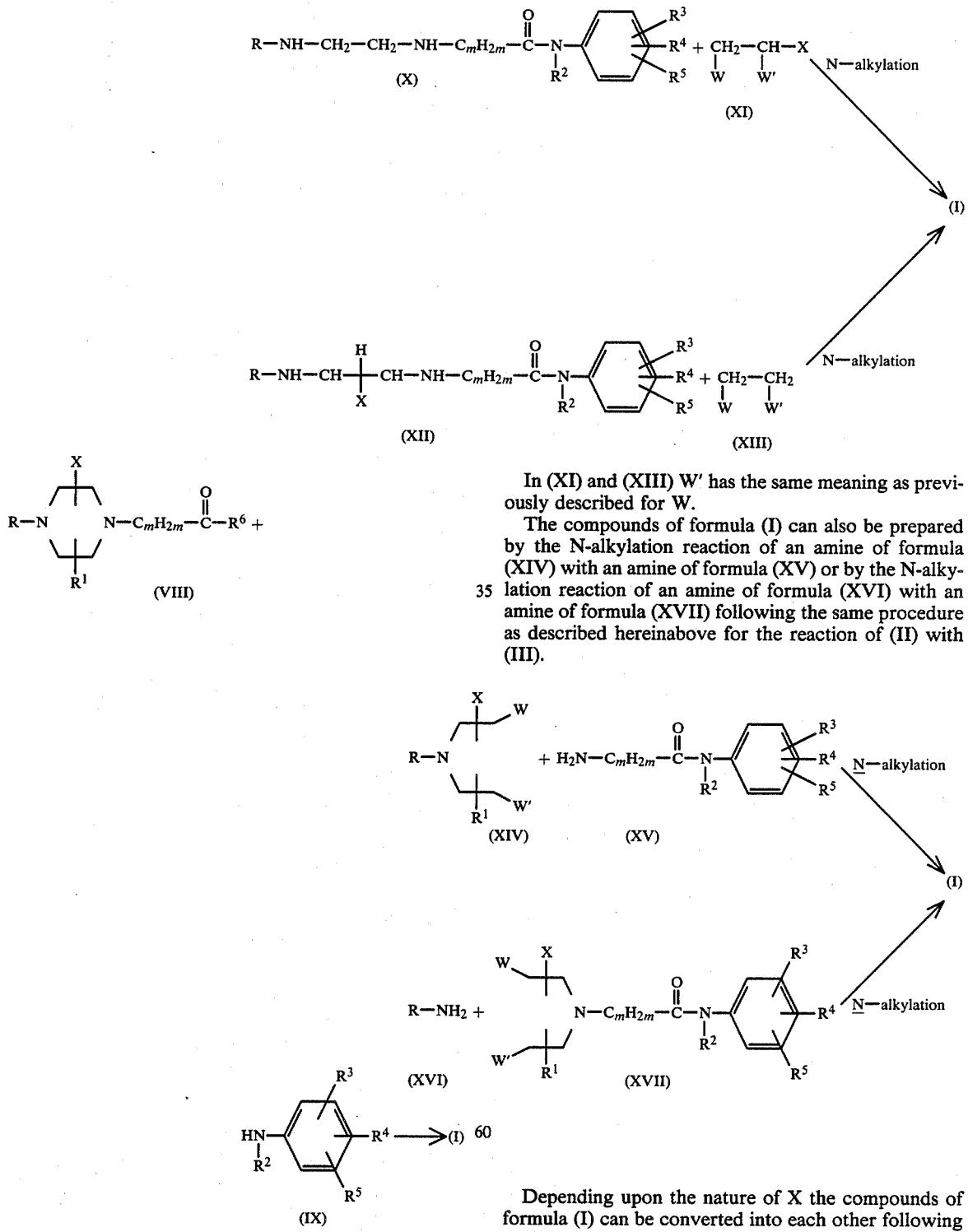

In (XI) and (XIII) W' has the same meaning as previously described for W.

The compounds of formula (I) can also be prepared by the N-alkylation reaction of an amine of formula (XIV) with an amine of formula (XV) or by the N-alkylation reaction of an amine of formula (XVI) with an amine of formula (XVII) following the same procedure as described hereinabove for the reaction of (II) with (III).

The compounds of formula (I) can even so be prepared by N-alkylating a diamine of formula (X) with a reagent of formula (XI) or by N-alkylating a diamine of Depending upon the nature of X the compounds of formula (I) can be converted into each other following art-known procedures of functional grouptransformations.

Some functional grouptransformations are illustrated in scheme 1 wherein the radical

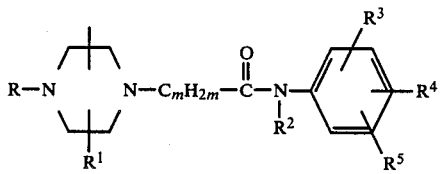

is represented by D.

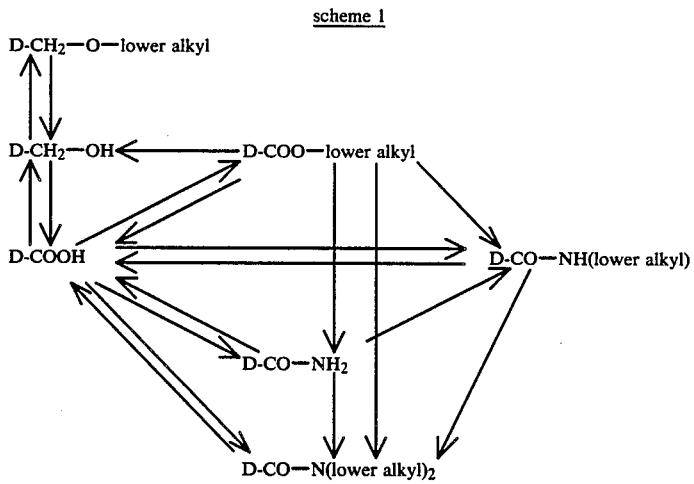

scheme 1

The carboxylic function may be converted into an ester function or an amide function following art-known procedures, e.g., by stirring and, if desired, heating the starting carboxylic acid with an appropriate alcohol, respectively, an apropriate amine. The carboxylic acid function may also be converted into an ester function by reacting the starting carboxylic acid with an appropriate alkyl halide in the presence of a base, e.g., sodium methoxide and the like. The ester function and the amide function may be converted into a carboxylic acid function by stirring and, if desired, heating the starting amide or ester into acidic- or alkaline aqueous medium. The ester function may be converted into an amide function by stirring and, if desired, heating the starting ester in the presence of an appropriate amine in a suitable reaction-inert solvent. The aminocarbonyl function may be converted into a mono- or di(lower alkyl)aminocarbonyl function and a lower alkylaminocarbonyl function may be converted into a di(lower alkyl)aminocarbonyl function by stirring and, if desired, heating the starting aminocarbonyl compound, respectively, lower alkylaminocarbonyl compound, with an appropriate lower alkyl halide following art-known N-alkylating procedures.

The carboxylic acid function and the ester function may be converted into an alcohol function following art-known reduction procedures such as, for example, with metal hydrides, diborane and the like. The alcohol function can be converted into a carboxylic acid function following art-known alcohol-to-carboxylic acid oxidizing procedures, e.g., with potassium permanganate, chromic trioxide, silver oxide and the like.

The alcohol function can be converted into an ether function following art-known procedures, e.g., by reacting the starting alcohol with an appropriate alkyl halide in the presence of a suitable base such as sodium hydride and the like in a suitable reaction-inert solvent. The ether function can be converted into an alcohol function following art-known ether-cleavage procedures, e.g., by reacting the starting ether with a strong Lewis acid, such as, for example, boron trifluoride and the like.

Depending upon the nature of R, $R^1$, $R^2$ and $R^3$ the compounds of formula (I) can also be converted into each other following art-known procedures of functional grouptransformation. For example, the compounds of formula (I) wherein at least one of $R^3$ and $R^4$ contains a nitro radical, can be converted into the corresponding amine derivatives following art-known nitro-to-amine reducing procedures, e.g., by catalytic reduction in the presence of an appropriate catalyst such as, for example, platinum-on-charcoal and the like.

The compounds of formula (I) may be converted to the therapeutically active non-toxic acid addition salt forms by treatment with an appropriate acid, such as, for example, an inorganic acid, such as hydrohalic acid, e.g., hydrochloric, hydrobromic and the like, and sulfuric acid, nitric acid, phosphoric acid and the like; or an organic acid, such as, for example, acetic, propanoic, 2-hydroxyacetic, 2-hydroxypropanoic, 2-oxopropanoic, propanedioic, butanediolic, (Z)-2-butenedioic, (E)-2-butenedioic, 2-hydroxybutanedioic, 2,3-dihydroxybutanedioic, 2-hydroxy-1,2,3-propanetricarboxylic, benzoic, 3-phenyl-2-propenoic, α-hydroxybenzeneacetic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids.

Conversely the salt form can be converted by treatment with alkali into the free base form.

It is obvious from formula (I) that the compounds of this invention have at least one asymmetric carbon atom in their structure, namely the piperazine carbon atom bearing the X-radical. This chiral center may be present in a R- and a S-configuration, this R- and S-notation being in correspondence with the rules described in R. S. Cahn, C. Ingold and V. Prelog in Angew. Chem. Int. Ed. Engl., 5, 385, 511 (1966). Consequently, the compounds of formula (I) may be present in two different enantiomeric forms, which may be separated from each other, for example, by converting the mixture of enantiomers into the acid addition salt form thereof with an optically active acid, separating the diastereomeric salts, e.g., by selective crystallization, and liberating the pure enantiomers by treatment with alkali.

When $R^1$ is other than hydrogen and/or the radicals R and $C_mH_{2m}$ have one or more additional chiral centers, each of these chiral centers may be present in the R- and the S-configuration and the compounds of formula (I) may have different diastereochemical forms, which may be separated from each other by physical separation methods such as, selective crystallization and chromatographic techniques, e.g., counter current distribution, column-chromatography and the like techniques.

In case $R^1$ is other than hydrogen, the substituents X and $R^1$ may be attached to the piperazine ring in a cis-relation to each other or in a trans-relation and then compounds of formula (I) are marked as "cis" respectively "trans".

The compounds of formula (I) wherein R is the radical (b) wherein Alk is a lower alkenediyl radical may be characterized by the notation "E" and "Z", said E- and Z-notation having the meanings described in J. Org. Chem., 35, 2849–2868 (1970).

Pure stereochemically isomeric forms may also be derived from the corresponding pure stereochemically isomeric forms of the appropriate starting materials, provided that the reaction occurs stereospecifically or highly stereoselectively.

In most compounds and starting materials the stereochemical configuration is not experimentally determined. In those cases it is conventionally agreed to designate the stereochemically isomeric form which is first isolated as "A" and the second as "B", without further reference to the actual stereochemical configuration.

Stereochemically isomeric forms of the compounds of formula (I) are naturally intended to be embraced within the scope of the invention.

A number of the intermediates and starting materials used in the foregoing preparations are known compounds, others may be prepared according to art-known methodologies of preparing similar compounds and for some of them synthetic methods are presented hereinafter.

The intermediates of formula (II) bearing the X radical in the 2-position of the piperazine ring, (II-a), the intermediates of formula (II) bearing the X radical in the 3-position of the piperazine ring, (II-b), the intermediates of formula (IV) bearing the X radical in α-position of the secondary amine function, (IV-a), and the intermediates of formula (IV), bearing the X radical in the β-position of the secondary amine function, (IV-b), can be derived from an appropriately substituted piperazine of formula (XVIII) as represented in scheme 2, wherein $P^1$ and $P^2$ represent each a protective group.

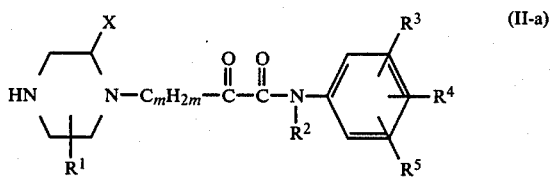

(II-a)

-continued

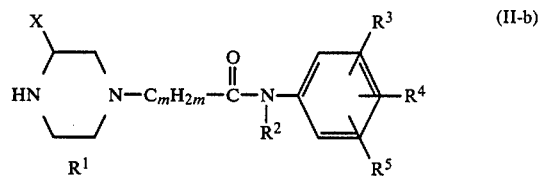

(II-b)

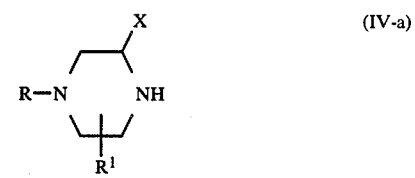

(IV-a)

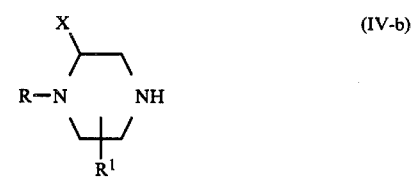

(IV-b)

The intermediates of formula (II-a) and (IV-b) may be derived from (XVIII) by reacting the latter with a reagent of formula LW, wherein L is R, respectively $L_1$, as defined in scheme 2, following art-known N-alkylating procedures as previously described for the preparation of (I) starting from (II) and (III) and, subsequently, eliminating the protective group $P^1$ in the thus obtained (XIX) following art-known procedures.

The intermediates of formula (II-b) and (IV-a) may be derived from (XVIII) by (i) protecting the secondary amine function with a $P^2$ radical, (ii) eliminating the protective group $P^1$ of the thus obtained (XX), (iii) reacting the so formed (XXI) with a reagnet of formula LW, wherein L is $L_1$, respectively R, following art-known N-alkylating procedures as previously described for the reaction of (II) with (III), and (iv) eliminating the protective group $P^2$ of the thus obtained (XXII) following art-known procedures.

Suitable protective groups are, for example, optionally substituted phenylmethyl radicals, optionally substituted lower alkylcarbonyl or arylcarbonyl radicals and the like. As can be seen in the reactionstep (XX)→(XXI) the protective groups $P^1$ and $P^2$ should be selected so that $P^1$ can be eliminated without effecting $P^2$. Suitable protective groups are, for example, hydrogenolyzable groups as $P^2$ radicals, e.g., the phenylmethyl group and the like, and hydrolyzable groups as $P^1$ radicals, e.g., the trifluoroacetyl group and the like.

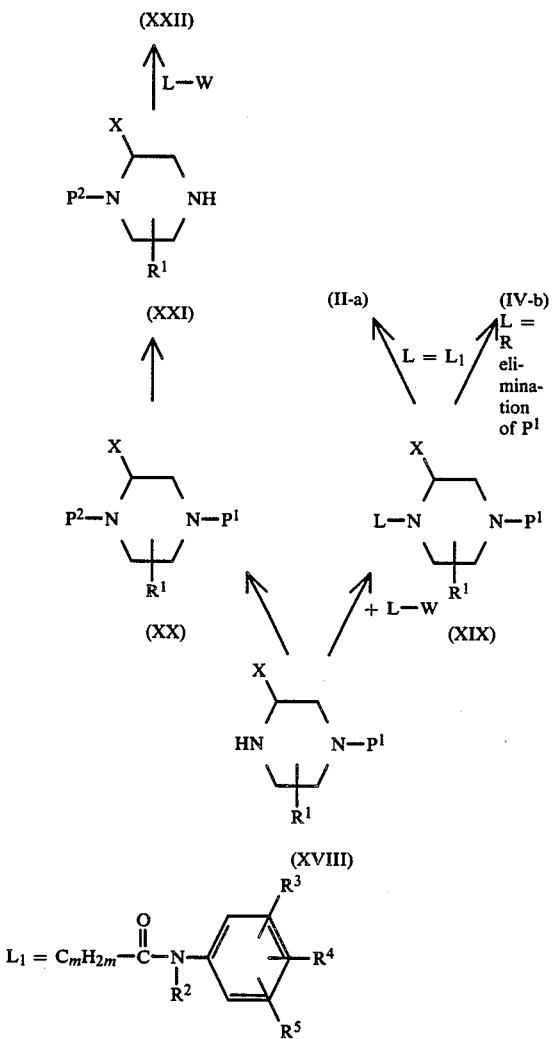

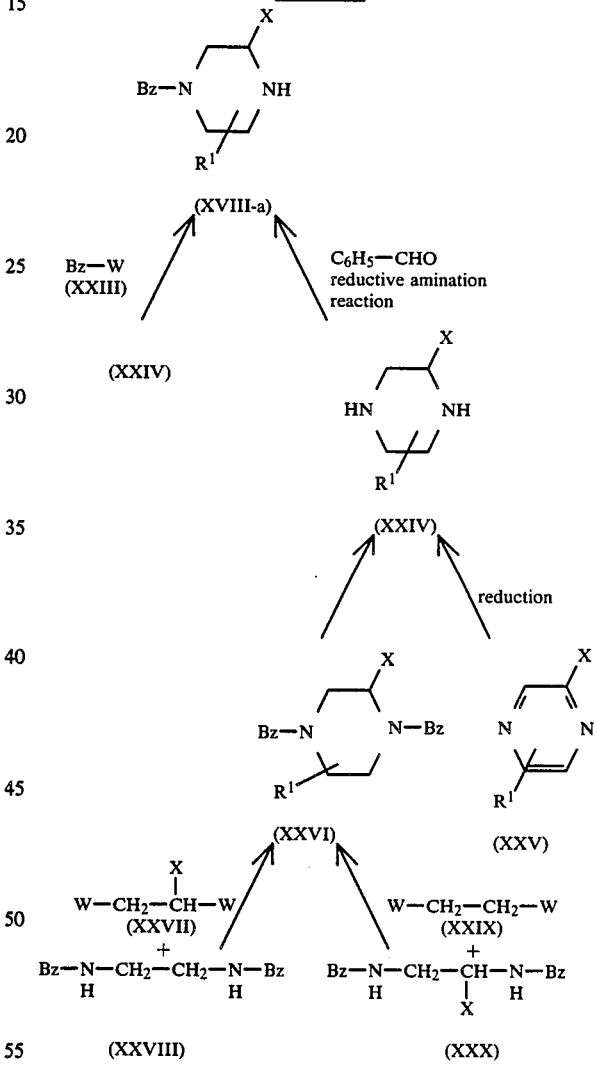

(XXIV) may be derived from the corrresponding pyrazines (XXV) following art-known catalytic hydrogenation reaction procedures or by the hydrogenolysis reaction of the corresponding di(phenylmethyl)piperazines (XXVI), which in turn may be prepared by reacting (XXVII) with (XXVIII) or (XXIX) with (XXX) following the same procedure as previously described for the preparation of (I) starting from (X) and (XI) or (XII) and (XIII).

In scheme 3 the 1,2-ethanediyl radical in (XXVII) or (XXVIII) and (XXIX) or (XXX) is substituted with a radical having the meaning of $R^1$.

The piperazines (XVIII), used as a starting materials in scheme 2, may be prepared following art-known procedures. For example, the piperazines (XVIII) wherein $P^1$ is a phenylmethyl radical, (XVIII-a) may be prepared, as shown in scheme 3, by reacting an appropriately substituted piperazine (XXIV) with a reagent (XXIII) following art-known N-alkylating procedures as described hereinabove, or by reacting an appropriately substituted piperazine (XXIV) with benzaldehyde following art-known reductive amination reaction procedures, i.e., by stirring and heating the reactants together in the presence of a suitable catalyst, e.g., platinum-on-charcoal, in a suitable reaction-inert solvent under hydrogen atmosphere. The starting piperazines The intermediates of formula (II-b) and (IV-a) wherein X is a radical of formula —$(CH_2)_p$—(CO)-$_q$—ZH, wherein Z is O or $NR^7$, said $R^7$ being hydrogen or lower alkyl, p is 0 or 1 and q is 0 or 1, provided that the sum of p and q is 1 when Z is $NR^7$, said intermediates being represented by the formulae (II-b-1), respectively (IV-a-1), may also be prepared starting from a piperazine (XXXI) by (i) stirring and, if desired, heating (XXXI) and a carbonyl derivative (XXXII), wherein $R^8$ and $R^9$ are each, independently from each other, hydrogen or lower alkyl, in a suitable reaction-inert solvent, e.g., methoxyethanol and the like; if desired, in the presence of a suitable base; (ii) reacting the thus obtained (XXXIII) with a reagent of formula LW, wherein L is $L_1$, or R, following art-known N-alkylating procedures as previously described for the preparation of (I) starting from (II) and (III); and (iii) hydrolyzing the thus obtained (XXXIV) in acidic aqueous medium.

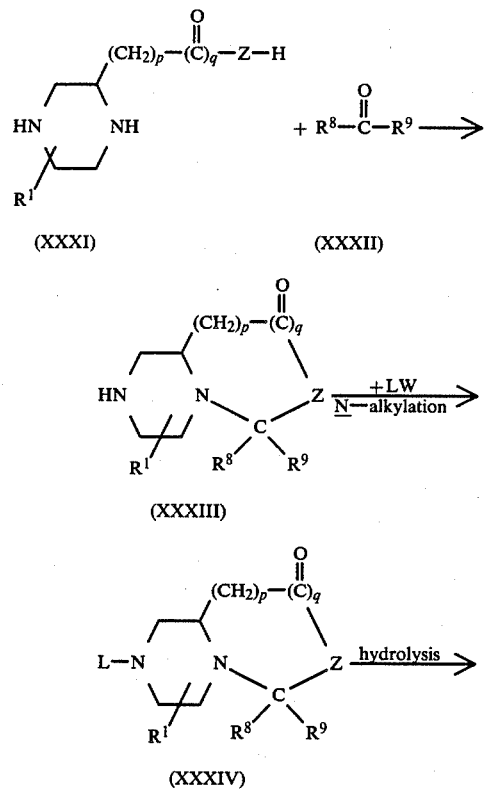

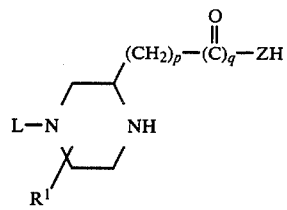

L = $L_1$ (II-b-1)
L = R (IV-a-1)

The intermediates of formula (III) can be prepared following the same procedures as those described in U.S. Pat. No. 3,714,159.

The preparations of the intermediates of formulae (VI), (VIII), (X), (XII), (XIV) and (XVI) starting from (III) are shown in scheme 4.

The intermediates of formula (XIV), (VI), (VIII) and (XVI) can be derived from (III) by reacting the latter with the amines (XXXV), respectively (XXXVIII), (XXXIX) and $NH_3$ following art-known N-alkylating procedures as described hereinabove for the preparation of (I) starting from (II) and (III). The intermediate of formula (VI) and (VIII) can also be prepared by the N-alkylation reaction of (XIV) with an amine of formula (XXXVI), respectively (XXXVII). The intermediate of formula (X) and (XII) and also the intermediates of formula (VI) and (VIII) can be prepared by the N-alkylation of (XVI) with (XL), respectively, (XLI), (XLII) and (XLIII).

In scheme 4 the 1,2-ethanediyl radical in (XL), (X), (XLI) and/or (XII) may be substituted with a radical having the meaning of $R^1$.

Scheme 4

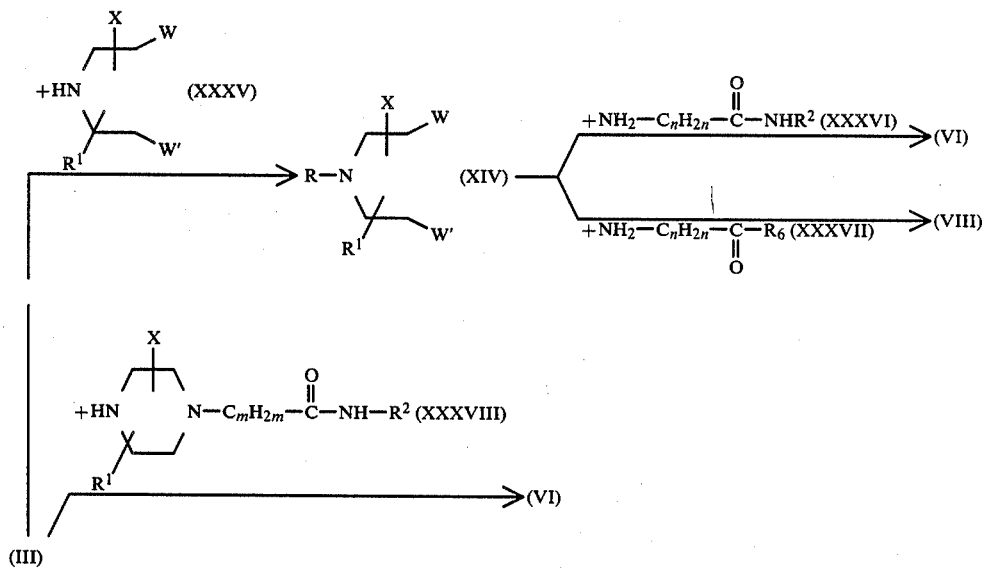

Scheme 4

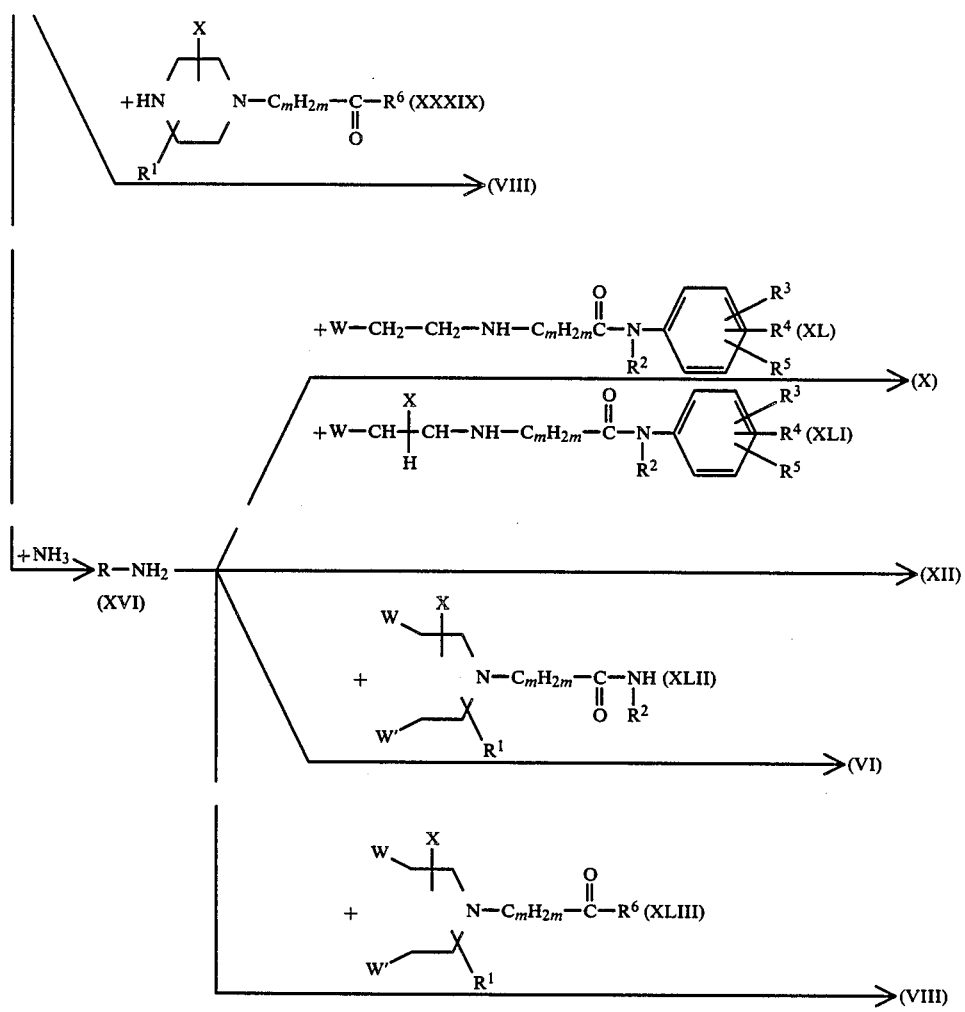

The intermediates of formula (V) can be prepared by the N-alkylation reaction of an appropriate acid halide (XLIV) with an aniline (IX).

The intermediates of formula (XV) and (XVII) can in turn be derived from (V) by reacting the latter with ammonia, respectively an amine (XLV) following art-known N-alkylating procedures.

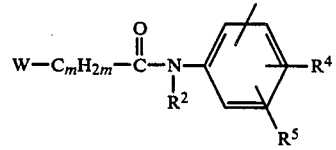

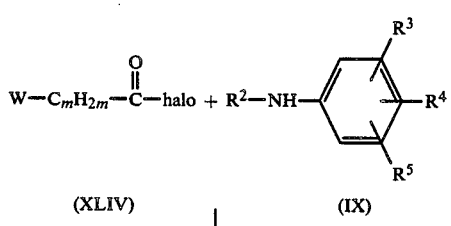

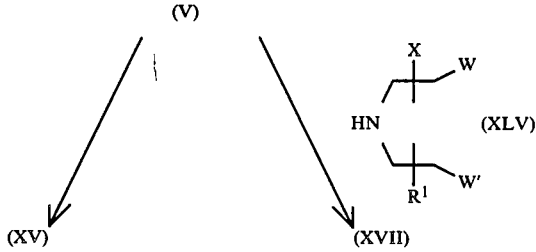

The functional grouptransformation procedures, as described in scheme 1, may also be carried out on all the intermediates having the radical X in their structure.

The compounds of formula (I), their pharmaceutically acceptable acid addition salts and the stereochemically isomeric forms thereof, when intravenously or orally administered to vertebrates, increase the oxygen tension (pO$_2$) of the coronary sinus venous blood. Said pO$_2$ increase is evidenced by the experimental data obtained in the coronary sinus venous pO$_2$-test in the anesthetized dog, which is described in The Journal of Pharmacology and Experimental Therapeutics, 152, (2), 265-274 (1966).

Coronary sinus venous pO$_2$ in the anesthetized dog

A cardiac catheter was advanced into the coronary sinus of the anesthetized dog and oxygen tension (pO$_2$ in mm Hg) of the venous coronary blood was measured with the Gleichmann-Lubbers modification of the Clark electrode, housed in a contant blood flow cuvette.

The pO$_2$ values were read off the calibrated scale of a light-spot galvanometer. Aortic blood pressure, respiratory rate and electro-cardiogram were recorded throughout the experiment. The animals breathed spantaneously. After a control periof of 30 min. a steady state was usually obtained. At this point a dose of the active compound was given by slow intravenous injection. Subsequent intravenous doses of other active compounds were injected at the end of each new steady state period of not less than 10 min.

Tables 1 and 2 show the lowest effective intravenous dose (in mg/kg body weight) whereby the pO$_2$ in the coronary sinus was increased by 100% as compared to the control value (column 1) and the duration of action at said lowest effective dose (column 2).

The data, illustrated in tables 1 and 2, are intended to illustrate and not to limit the scope of the present invention.

TABLE I $$R-N\underset{X}{\overset{\phantom{X}}{\bigcirc}}N-C_mH_{2m}-\overset{O}{\underset{\|}{C}}-\underset{R^2}{N}-aryl$$

| R | X | $C_mH_{2m}$ | $R^2$ | aryl | Isomeric form | Base or Salt | LED in mg/kg body weight column 1 | duration of action column 2 |
|---|---|---|---|---|---|---|---|---|
| (4-F—C₆H₄)₂CH—(CH₂)₃— | 2-CONH₂ | CH₂ | H | 2,6-(CH₃)₂—C₆H₃— | — | base | 0.31 | 30' |
| (4-F—C₆H₄)₂CH—(CH₂)₃— | 3-CONH₂ | CH₂ | H | 2,6-(CH₃)₂—C₆H₃— | — | 2 (COOH)₂ | 0.08 | >120' |
| (4-F—C₆H₄)₂CH—(CH₂)₃— | 2-CH₂OCH₃ | CH₂ | H | 2,6-(CH₃)₂—C₆H₃— | — | 2 HCl.H₂O | 2.5 | >100' |
| (4-F—C₆H₄)₂CH—(CH₂)₃— | 3-CONH₂ | CH₂ | H | 2,6-Cl₂—C₆H₃— | — | 2 HCl.H₂O | 0.04 | >70' |
| (4-F—C₆H₄)₂CH—(CH₂)₃— | 3-CONH₂ | CH₂ | H | 2-Cl, 6-(OCH₃)₂—C₆H₃— | — | 2 HCl | 0.08 | 190' |
| (4-F—C₆H₄)₂CH—(CH₂)₃— | 3-CONH₂ | CH₂ | H | 2,5-(OCH₃)₂—C₆H₃— | — | 2 HCl | 0.63 | 190' |
| (4-F—C₆H₄)₂CH—(CH₂)₃— | 3-CONH₂ | CH₂ | H | 2,6-Br₂—C₆H₃— | — | base | 0.04 | >110' |
| (4-F—C₆H₄)₂CH—(CH₂)₃— | 3-CONH₂ | CH₂ | H | 2-OCH₃, 5-CH₃—C₆H₃ | — | base | 1.25 | 40' |
| (4-F—C₆H₄)₂CH—(CH₂)₃— | 3-CON(CH₃)₂ | CH₂ | H | 2,5-(CH₃)₂—C₆H₃— | — | 2 HCl.H₂O | 0.63 | >220' |
| (4-F—C₆H₄)₂CH—(CH₂)₃— | 3-CONH₂ | CH₂ | H | 2,6-(CH₃)₂—C₆H₃— | — | 2 HCl.2 H₂O | 2.5 | 25' |
| (4-F—C₆H₄)₂CH—(CH₂)₃— | 3-CONH₂ | CH₂ | H | 2-C₂H₅—C₆H₄— | — | base | 0.63 | 110' |
| (4-F—C₆H₄)₂CH—(CH₂)₃— | 3-CONH₂ | CH₂ | CH₃ | 2,6-(CH₃)₂—C₆H₃— | — | 2 HCl.2 H₂O | 1.25 | 40' |
| (4-F—C₆H₄)₂CH—(CH₂)₃— | 3-CONH₂ | CH₂ | H | 2-(CO—CH₃)—C₆H₄— | — | base | 0.16 | >80' |
| (4-F—C₆H₄)₂CH—(CH₂)₃— | 3-CONHCH₃ | CH₂ | H | 2,6-(CH₃)₂—C₆H₃— | — | 2 HCl | 0.31 | >130' |
| (4-F—C₆H₄)₂CH—(CH₂)₃— | 3-CONH₂ | CH₂ | H | 2-CF₃—C₆H₄— | — | base | 2.5 | 30' |
| (4-F—C₆H₄)₂CH—(CH₂)₃— | 3-CONH₂ | CH₂ | H | 2-OCH₃—C₆H₄— | — | 2 HCl.½ H₂O | 1.25 | 100' |
| (4-F—C₆H₄)₂CH—(CH₂)₃— | 3-CONH₂ | CH₂ | H | 2,6-(CH₃)₂—C₆H₃— | — | (+)-[R—(R*,R*)] 1½ HOOC—CH(OH)—CH(OH)—COOH.H₂O | 0.31 | 80' |
| (4-F—C₆H₄)₂CH—(CH₂)₃— | 3-CONH₂ | CH₂—CH₂— | H | 2-OCH₃, 5-CF₃—C₆H₃— | — | base | 1.25 | 50' |
| (4-F—C₆H₄)₂CH—(CH₂)₃— | 3-CONH₂ | CH₂ | H | 2,6-(CH₃)₂—C₆H₃— | — | base | 2.5 | 25' |
| (4-F—C₆H₄)₂CH—(CH₂)₃— | 3-CONH₂ | CH₂ | H | 2-CH₃, 4-NH₂—C₆H₃— | — | base | 0.08 | 90' |
| (4-F—C₆H₄)₂CH—(CH₂)₃— | 3-CONH₂ | CH₂ | H | 2,6-F₂—C₆H₃— | — | base | 0.16 | >170' |
| (4-F—C₆H₄)₂CH—(CH₂)₃— | 3-CONH₂ | —CH(CH₃)— | H | 2-CH₃, 5-F—C₆H₃— | — | 2 HCl.H₂O | 0.16 | 20' |
| (4-F—C₆H₄)₂CH—(CH₂)₃— | 3-CONH₂ | CH₂ | H | 2-CH₃, 4-NO₂—C₆H₃— | — | 2 HCl.H₂O | 0.31 | 80' |
| (4-F—C₆H₄)₂CH—(CH₂)₃— | 3-CONH₂ | —CH₂—CH₂— | H | 2,6-Cl₂—C₆H₃— | — | 2 HCl.H₂O | 0.63 | 190' |
| (4-F—C₆H₄)₂CH—(CH₂)₃— | 3-CONH₂ | —CH(CH₃)— | H | 2,6-(CH₃)₂—C₆H₃— | — | base | 2.5 | 110' |
| (4-F—C₆H₄)₂CH—(CH₂)₃— | 2-CONH₂ | CH₂ | H | 2-CH₃, 5-Cl—C₆H₃— | — | base | 0.63 | 120' |
| (4-F—C₆H₄)₂CH—(CH₂)₃— | 2-CONH₂ | CH₂ | H | 2,6-Cl₂—C₆H₃— | — | 2 HCl.H₂O | 2.5 | 80' |
| (4-F—C₆H₄)₂CH—(CH₂)₃— | 2-CONH₂ | CH₂ | H | 2-Cl—C₆H₄— | A | base | 1.25 | 25' |
| (4-F—C₆H₄)₂CH—(CH₂)₃— | 2-CONH₂ | CH₂ | H | 2-CH₃, 5-Cl—C₆H₃— | — | base | 0.63 | 40' |
| (4-F—C₆H₄)₂CH—(CH₂)₃— | 2-CH₂O—CH₂—CH₃ | 3-CONH₂ | H | 2,6-(CH₃)₂—C₆H₃— | — | base | 2.5 | 70' |
| (4-F—C₆H₄)₂CH—(CH₂)₃— | 2-CONH₂ | —CH(CH₃)— | H | 2,5-(CH₃)₂—C₆H₃— | — | 2 HCl.½ H₂O | 1.25 | 70' |
| (4-F—C₆H₄)₂CH—(CH₂)₃— | 2-CONH₂ | CH₂ | H | 2,5-Cl₂—C₆H₃— | — | 2 HCl | 1.25 | 180' |
| (4-F—C₆H₄)₂CH—(CH₂)₃— | 2-CONH₂ | —CH₂—CH₂— | H | 2,6-(CH₃)₂—C₆H₃— | — | base | 1.25 | 25' |
| (4-F—C₆H₄)₂CH—(CH₂)₃— | 2-CONH₂ | CH₂ | H | 2-Cl, 6-CH₃—C₆H₃— | — | base | 1.25 | 50' |
| (4-F—C₆H₄)₂CH—(CH₂)₃— | 2-CONHCH₃ | CH₂ | H | 2,6-(CH₃)₂—C₆H₃— | — | base | 2.5 | >30' |
| (4-F—C₆H₄)₂CH—(CH₂)₃— | 2-CONH₂ | CH₂ | H | 2-CH₃, 5-F—C₆H₃— | — | 2 HCl | 0.63 | 15' |
| (4-F—C₆H₄)₂CH—(CH₂)₃— | 2-CONH₂ | CH₂ | H | 2,6-Cl₂—C₆H₃— | — | base | 0.63 | 25' |
| (4-F—C₆H₄)₂CH—(CH₂)₃— | 2-CONH₂ | CH₂ | H | 2-CH₃, 4-CH₃O—C₆H₃— | — | base | 0.63 | 90' |
| (4-F—C₆H₄)₂CH—(CH₂)₃— | 2-CONH₂ | —CH₂—CH₂— | H | 2,6-Cl₂—C₆H₃— | — | base | 2.5 | 120' |

TABLE I-continued $$\text{R-N}\overbrace{\phantom{XXXXX}}^{X}\text{N-C}_mH_{2m}-\overset{\overset{O}{\|}}{C}-\underset{\underset{R^2}{|}}{N}-\text{aryl}$$

| R | X | $C_mH_{2m}$ | $R^2$ | aryl | Isomeric form | Base or Salt | LED in mg/kg body weight | duration of action |
|---|---|---|---|---|---|---|---|---|
| $\underset{(4\text{-}F\text{-}C_6H_4)_2-\overset{|}{C}-(CH_2)_3-}{COOC_2H_5}$ | 2-CH₂OH | CH₂ | H | 2,6-Cl₂—C₆H₃— | — | base | 2.5 | 60' |
| (4-F—C₆H₄)₂—CH—(CH₂)₃— | 3-CONH₂ | CH₂ | H | 2-CH₃, 4-OCH₃—C₆H₃— | — | base | 0.31 | >100' |
| (4-F—C₆H₄)₂CH—(CH₂)₃— | 2-CH₂CONH₂ | CH₂ | H | 2,6-(CH₃)₂—C₆H₃— | — | base | 1.25 | 40' |
| $\underset{(4\text{-}F\text{-}C_6H_4)_2C-(CH_2)_3-}{CN}$ | 2-CH₂OH | CH₂ | H | 2,6-(CH₃)₂—C₆H₃— | — | 2 HCl | 1.25 | 30' |
| (4-F—C₆H₄)₂CH—(CH₂)₃— | 2-CH₂OH | CH₂ | H | 2,6-(CH₃)₂, 4-NO₂—C₆H₂— | — | base | 2.5 | >30' |
| (4-F—C₆H₄)₂CH—(CH₂)₃— | 2-CONH—CH₂CH₂OH | CH₂ | H | 2,6-(CH₃)₂—C₆H₃— | — | 2 HCl | 2.5 | 10' |
| (4-F—C₆H₄)₂CH—(CH₂)₃— | 3-CONH—CH(CH₃)₂ | CH₂ | H | 2,6-(CH₃)₂—C₆H₃— | — | 2 HCl | 2.5 | 40' |
| (4-F—C₆H₄)₂CH—(CH₂)₃— | 2-CONH—CH(CH₃)₂ | CH₂ | H | 2,6-(CH₃)₂—C₆H₃— | — | base | 2.5 | 100' |
| (4-F—C₆H₄)₂CH—(CH₂)₃— | 2-CONH—CH₂CH₂OH | CH₂ | H | 2,6-Cl₂—C₆H₃— | — | ½ H₂O | 2.5 | >40' |
| (4-F—C₆H₄)₂CH—(CH₂)₃— | 2-CH(CH₃)—OH | CH₂ | H | 2,6-(CH₃)₂—C₆H₃— | — | 2 HCl.H₂O | 1.25 | 40' |
| (4-F—C₆H₄)₂CH—(CH₂)₃— | 3-CONH—CH₃ | CH₂ | H | 2,6-(CH₃)₂, 4-NO₂—C₆H₂— | — | base | 1.25 | 45' |
| (4-F—C₆H₄)₂CH—(CH₂)₃— | 3-CH₂OH | CH₂ | H | 2,6-(CH₃)₂, 4-NH₂—C₆H₂— | — | base | 0.04 | >120' |
| (4-F—C₆H₄)₂CH—(CH₂)₃— | 3-CH₂OH | CH₂ | H | 2,6-Cl₂—C₆H₃— | — | base | 2.5 | 50' |
| (4-F—C₆H₄)₂CH—(CH₂)₃— | 2-CONHCH₃ | CH₂ | H | 2-Cl, 6-CH₃—C₆H₃— | — | base | 0.31 | 40' |
| (4-F—C₆H₄)₂CH—(CH₂)₃— | 3-CONH₂ | CH₂ | H | 2,6-(CH₃)₂, 4-NH₂—C₆H₂— | — | base | 2.5 | 70' |
| (4-F—C₆H₄)₂CH—(CH₂)₃— | 3-CH₂OH | CH₂ | H | 2,6-(iC₃H₇)₂—C₆H₃— | — | 2 HCl.H₂O | 2.5 | 30' |
| (4-F—C₆H₄)₂CH—(CH₂)₃— | 3-CH₂OH | CH₂ | H | 2-CH₃, 5-F—C₆H₃— | — | 2 HCl | 2.5 | 70' |
| (4-F—C₆H₄)₂CH—(CH₂)₃— | 2-CH(CH₃)—OCH₃ | CH₂ | H | 2,6-(CH₃)₂, 4-NH₂—C₆H₂— | A | base | 1.25 | 25' |
| (4-F—C₆H₄)₂CH—(CH₂)₃— | 3-CONH₂ | CH₂ | H | 2,6-(CH₃)₂—C₆H₃— | — | (COOH)₂ | 2.5 | 70' |
| (4-F—C₆H₄)₂CH—(CH₂)₃— | 3-CONHCH₃ | CH₂ | H | 2-C₂H₅, 6-CH₃—C₆H₃— | — | 2 HCl.H₂O | 0.31 | 90' |
| (4-F—C₆H₄)₂CH—(CH₂)₃— | 2-CH₂OH | CH₂ | H | 2-Cl, 6-CH₃—C₆H₃— | — | 2 HCl | 0.31 | 50' |
| (4-F—C₆H₄)₂CH—(CH₂)₃— | 2-CONHCH₃ | CH₂ | H | 2-Cl, 6-CH₃—C₆H₃— | — | base | 0.63 | 10' |
| (4-F—C₆H₄)₂CH—(CH₂)₃— | 3-CONH₂ | CH₂ | H | 2,6-(CH₃)₂, 4-NH₂—C₆H₂— | — | 2 HCl | 0.31 | 70' |
| (4-F—C₆H₄)₂CH—(CH₂)₃— | 2-CONHCH—CH₃ | CH₂ | H | 2-CH₃, 4-NH₂—C₆H₃— | — | base | 0.31 | >110' |
| (4-F—C₆H₄)₂CH—(CH₂)₃— | 3-CONHCH₃ | CH₂ | H | 2,4,6-(CH₃)₃—C₆H₂— | — | base | 1.25 | 50' |
| (4-F—C₆H₄)₂CH—(CH₂)₃— | 3-CONHCH₃ | CH₂ | H | 2-COCH₃—C₆H₄— | — | base | 0.63 | >80' |
| (4-F—C₆H₄)₂CH—(CH₂)₃— | 3-CONHCH₃ | CH₂ | H | 2,6-(CH₃)₂, 4-NH₂—C₆H₂— | — | base | 0.31 | >80' |
| (4-F—C₆H₄)₂CH—(CH₂)₃— | 3-CONH₂ | CH₂ | H | 2-COOCH₃—C₆H₄— | — | base | 0.31 | >170' |
| (4-F—C₆H₄)₂CH—(CH₂)₃— | 2-CONH₂ | CH₂ | H | 2,4,6-(CH₃)₃—C₆H₂— | — | base | 1.25 | 50' |
| (4-F—C₆H₄)₂CH—(CH₂)₃— | 3-CONH₂ | CH₂ | H | 2-CH₃, 4-NO₂—C₆H₃— | — | base | 0.63 | 10' |
| (4-F—C₆H₄)₂CH—(CH₂)₃— | 2-CONHCH₃ | CH₂ | H | 2-CH₃, 5-Cl—C₆H₃— | — | 2HCl | 2.5 | >70' |
| (4-F—C₆H₄)₂CH—(CH₂)₃— | 3-CONHCH₃ | CH₂ | H | 2,6-Cl₂, 4-CN—C₆H₂— | — | base | 1.25 | 110' |
| (4-F—C₆H₄)₂CH—(CH₂)₃— | 3-CONH₂ | CH₂ | H | 2,6-Cl₂, 4-NH₂—C₆H₂— | — | 2 HCl | 0.16 | >180' |
| (4-F—C₆H₄)₂CH—(CH₂)₃— | 3-CONH₂ | CH₂ | H | 2,6-Cl₂, 4-NH₂—C₆H₂— | — | 2 HCl.2H₂O | 0.08 | >280' |

TABLE 2

$$R-N\underset{R^1}{\overset{X}{\diagup\!\!\!\!\diagdown}}N-CH_2-\underset{\phantom{.}}{\overset{O}{\overset{\|}{C}}}-NH-\text{aryl}$$

| R | X | $R^1$ | aryl | isom. form | base/salt form | column 1<br>LED mg/kg body weight | column 2<br>duration of action |
|---|---|---|---|---|---|---|---|
| 2-(4-F—$C_6H_4$—CO),4-F—$C_6H_3$—O—$(CH_2)_3$— | 3-$CONH_2$ | H | 2,6-$(CH_3)_2$—$C_6H_3$— | — | HCl | 1.25 | 30' |
| (4-F—$C_6H_4)_2$CH—$CH_2$—CH(OH)—$CH_2$— | 3-$CONH_2$ | H | 2,6-$(CH_3)_2$—$C_6H_3$— | — | base | 0.63 | >50' |
| (4-F—$C_6H_4)_2$CH—NH—CO—$CH_2$— | 3-$CONH_2$ | H | 2,6-$(CH_3)_2$—$C_6H_3$— | — | base | 2.5 | >160' |
| 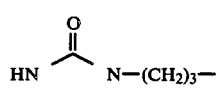 | 3-$CONH_2$ | H | 2,6-$(CH_3)_2$—$C_6H_3$— | — | base | 2.5 | 100' |
| (4-F—$C_6H_4)_2$CH—$(CH_2)_3$— | 3-$CONH_2$ | H | 2,6-$(CH_3)_2$—$C_6H_3$— | — | 2 HCl | 1.25 | 180' |
| (4-F—$C_6H_4)_2$CH—$(CH_2)_3$— | 3-$CONH_2$ | H | 2,6-$(CH_3)_2$, 4-OH—$C_6H_2$— | — | 2 HCl.$H_2O$ | 0.08 | >80' |
| (4-F—$C_6H_4)_2$CH—$(CH_2)_3$— | 3-$CONH_2$ | H | 2,6-$(CH_3)_2$, 4-NH—i.$C_3H_7$—$C_6H_2$— | — | $H_2O$ | 1.25 | >130' |
| (4-F—$C_6H_4)_2$CH—$(CH_2)_3$— | 3-$CONH_2$ | H | 2,6-$(CH_3)_2$, 4-(NH—CO—$NH_2$)—$C_6H_2$— | — | base | 0.04 | >110' |
| (4-F—$C_6H_4)_2$CH—$(CH_2)_3$— | 3-$CONH_2$ | H | 2,6-$(CH_3)_2$, 4-(NH—CO—$C_2H_5$)—$C_6H_2$— | — | $H_2O$ | ~0.63 | >25' |
| (4-F—$C_6H_4)_2$CH—$(CH_2)_3$— | 3-$CONH_2$ | H | 2,6-$(CH_3)_2$, 4—$NMe_2$—$C_6H_2$— | — | 3 HCl.$H_2O$ | 0.16 | 70' |
| (4-F—$C_6H_4)_2$CH—$(CH_2)_4$— | 3-$CONH_2$ | H | 2,6-$Cl_2$—$C_6H_3$— | — | 2 HCl.$H_2O$ | 0.16 | >300' |
| (4-F—$C_6H_4)_2$CH—$(CH_2)_3$— | 3-$CONH_2$ | H | $C_6H_5$— | — | 2 HCl | 0.63 | 140' |
| (4-F—$C_6H_4)_2$CH—$(CH_2)_3$— | 3-$CONH_2$ | H | 4-$NH_2$—$C_6H_4$— | — | 2 HCl.$H_2O$ | 0.63 | 100' |
| (4-F—$C_6H_4)_2$CH—$(CH_2)_3$— | 3-$CONH_2$ | H | 4-$NMe_2$—$C_6H_4$— | — | $H_2O$ | 0.63 | >130' |
| 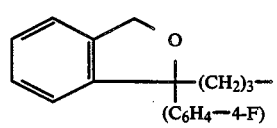 | 3-$CONH_2$ | H | 2,6-$Cl_2$—$C_6H_3$— | — | 2 HCl.$H_2O$ | 0.63 | 160' |
| (4-F—$C_6H_4)_2$CH—$(CH_2)_2$— | 3-$CONH_2$ | H | 2,6-$Me_2$—$C_6H_3$ | — | base | 0.63 | >70' |
| $C_6H_5$—CH=CH—$CH_2$ | 2-$CONH_2$ | H | 2,6-$(CH_3)_2$—$C_6H_3$— | (E) | 2HCl.½ $H_2O$ | 1.25 | 150' |
| (4-F—$C_6H_4)_2$—CH—$(CH_2)_4$— | 3-$CONH_2$ | 2-$CH_3$ | 2,6-$Cl_2$—$C_6H_3$— | trans | 2 HCl.$H_2O$ | 2.5 | 75' |
| $(C_6H_5)_2N$—$(CH_2)_3$— | 3-$CONH_2$ | H | 2,6-$Cl_2$—$C_6H_3$— | — | ½ $CH_3$—CH(OH)$CH_3$ | 1.25 | >90' |
| (4-F—$C_6H_4$)(3-pyridinyl)—C=CH—$(CH_2)_2$— | 3-$CONH_2$ | H | 2,6-$Cl_2$—$C_6H_3$— | — | $H_2O$ | 0.04 | >150' |

The compounds of formula (I), their pharmaceutically acceptable acid addition salts and the stereochemically isomeric forms thereof, administered intravenously or orally, also exert a protective action against the consequences of complete normothermic ischaemia in dog hearts. The test, evidencing said protection, is described in "Myocardial Protection and Exercise Tolerance: the Role of Lidoflazine, a New Anti-anginal Agent.", Royal Society of Medecine International Congress and Symposium Series No. 29, p. 89–95 (1980).

Protection against normothermic myocardial ischaemia in the dog

Experiments were performed on adult anesthetized beagles with a body weight ranging between 9 and 15 kg.

Systemic blood pressure was measured via the left femoral artery, using a JF Millar tip manometer. A Swann-Ganz thermodilution catheter was inserted via the right femoral vein and placed in the pulmonary artery to measure cardiac output by thermodilution and central nervous pressure through the proximal lumen. The other femoral vein was cannulated to facilitate the injection of saline at room temperature. The right femoral artery was cannulated and connected to the arterial line of the cardiopulmonarybypass. The heart was exposed through a right thoracotomy and suspended in a pericardial cradle. The right atrium was cannulated for connection of the venous line of the heart lung machine. Left ventricular pressure was measured after insertion of a JF Millar tip manometer via a pulmonary vein.

For cardiopulmonary bypass, two occlusive roller pumps, a bubble oxygenator and a heat exchanger were used. The heart lung machine was primed with 2000 ml of fresh heparinized blood, obtained from a donor dog. Serial blood samples were taken during the experiment for monitoring $pO_2$, $pCO_2$ and pH. The left ventricle was vented through an apex cannula at the start of the coronary bypass, during ischaemic arrest, and throughout the subsequent 30 minutes reperfusion period.

The experimental design:

(a) intravenous route of administration

Approximately twenty five minutes after intravenous administration of the active compound, the animal was subjected to total cardiopulmonary bypass at 37° C. by clamping the ascending aorta for 60 minutes. At the beginning of the complete ischaemia an amount of the active compound was added to the whole blood content. During the full period of complete ischaemia, myocardial temperature was kept constant at 37° C. Whilst the heart was empty and at rest, the coronary artery was reperfused for 30 minutes. After 10 minutes of reperfusion, the heart was defibrillated. At the end of the reperfusion period, the dog was weaned from the cardiopulmonary bypass and functional parameters were recorded until the end of the experiment.

Table 3, column 1 shows the lowest effective intravenous dose (in mg/kg body weight) of the compound whereby the heart of the dog retook his normal functions after 60 minutes of complete ischaemia, while column 2 shows the total amount of the compound, added to the whole blood content.

(b) oral route of administration

The experimental procedures were the same as described for the intravenous route of administration, except that the active compound was administered orally and neither given intravenously nor added to the whole blood content.

Table 3, column 3, shows the lowest effective oral dose (in mg/kg body weight) of the compound whereby the heart of the dog retook its normal functions after 60 minutes of complete ischaemia.

The data, illustrated in table 3, are intended to illustrate and not to limit the scope of the present invention.

TABLE 3

F—C$_6$H$_4$—CH(—C$_6$H$_4$—F)—CH$_2$—CH$_2$—CH$_2$—N(piperidine with X)—N—CH$_2$—C(=O)—NH—aryl

| X | aryl | LED (i.v.) mg/kg body weight | mg. compound added to blood | LED (or) mg/kg body weight |
|---|---|---|---|---|
| 3-CONH$_2$ | 2,6-(CH$_3$)$_2$—C$_6$H$_3$— | 1.25 | 5 | — |
| 2-CONH$_2$ | 2,6-(CH$_3$)$_2$—C$_6$H$_3$— | 0.63 | 2.5 | 5 |
| 2-CONH$_2$ | 2,6-Cl$_2$—C$_6$H$_3$— | 0.16 | 0.63 | 2.5 |
| 2-CONH—CH$_3$ | 2,6-(CH$_3$)$_2$—C$_6$H$_3$— | 1.25 | 5 | — |
| 3-CH$_2$OCH$_3$ | 2,6-(CH$_3$)$_2$—C$_6$H$_3$— | 1.25 | 5 | — |
| 2-CH$_2$OCH$_3$ | 2,6-(CH$_3$)$_2$—C$_6$H$_3$— | 1.25 | 5 | — |

In view of their pharmacological activites the compounds of formula (I) are useful to ameliorate the blood perfusion of the muscular tissues of the heart and also to protect the heart, partially or completely, from myocardial injury caused by more or less brief episodes of ischaemia, anoxia or hypoxia and, as such, the subject compounds may, for example, be used in the cure of the prophylaxis of patients suffering from angina pectoris and of patients in a pre- or post myocard infarct stage by administering said compounds intravenously or orally.

The subject compounds may be formulated into various pharmaceutical forms for administration purposes. To prepare the pharmaceutical compositions of this invention, an effective amount of the particular compound, in base or acid-addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, preferably, for administration orally, rectally or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in adminstration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solutiblity, may be included. Injectable solution, for example, may be prepared in which the carrier comprises saline solution, glucose solution or a mixture of saline and glucose solution. Injectable suspensions may also be prepared in which case appropriate liquid carriers, suspending agents and the like may be employed. Acid addition salts of (I), due to their increased water solubility over the corresponding base form, are obviously more suitable in the preparation of aqueous compositions.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therpeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

The following formulations exemplify typical pharmaceutical compositions in dosage unit form suitable for systemic administration to patients in accordance with the present invention.

Oral drop: The following formulation provides 10 liters of an oral-drop solution comprising 5 milligrams of 3-(aminocarbonyl)-4-[4,4-bis(4-fluorophenyl)butyl]-N-(2,6-dichlorophenyl)-1-piperazineacetamide as the active ingredient per ml.

| A.I. | 50 grams |
| --- | --- |
| 2-Hydroxypropanoic acid | 2.5 milliliters |
| Methyl 4-hydroxybenzoate | 18 grams |
| Propyl 4-hydroxybenzoate | 2 grams |
| Pyrogen-free water q.s. ad 10 liters. | |

The methyl and propyl 4-hydroxybenzoates were dissolved in about 5 liters of boiling pyrogen-free water. After cooling to about 50° C. there were added while stirring the 2-hydroxypropanoic acid and thereafter the A.I. The solution was cooled to room temperature and supplemented with pyrogen-free water ad volume. The solution was sterilized by filtration (U.S.P. XVII p. 811) and filled in sterile containers.

Injectable solution: The oral drop solution described herebefore may be used as an injectable solution.

Capsules: 10,000 Hard gelatine capsules, each containing as the active ingredient (A.I.) 20 milligrams of 3-(aminocarbonyl)-4-[4,4-bis(4-fluorophenyl)butyl]-N-(2,6-dichlorophenyl)-1-piperazineacetamide, were prepared from the following composition:

| A.I. | 200 grams |
| --- | --- |
| Lactose | 1000 grams |
| Starch | 300 grams |
| Talc | 300 grams |
| Calcium stearate | 10 grams |

An uniform mixture of the active an supplementary ingredients was prepared and filled into two-piece hard gelatine capsules.

Tablets: 5000 Compressed tablets, each containing as the active ingredient (A.I.) 25 milligrams of 3-(aminocarbonyl)-4-[4,4-bis(4-fluorophenyl)butyl]-N-(2,6-dichlorophenyl)-1-piperazineacetamide, were prepared from the following formulation.

| A.I. | 125 grams |
| --- | --- |
| Starch | 150 grams |
| Dibasic calcium phosphate hydrous | 650 grams |
| Calcium stearate | 35 grams |

The finely powdered ingredients were mixed well and granulated with 10% starch paste. The granulation was dried and compressed into tablets.

Oral suspension: The following formulation provides 5 liters of an oral suspension comprising as an active ingredient (A.I.) 15 milligrams of 3-(aminocarbonyl)-4-[4,4-bis(4-fluorophenyl)butyl]-N-(2,6-dichlorophenyl)-1-piperazineacetamide per teaspoonfull (5-milliliters).

| A.I. | 15.0 grams |
| --- | --- |
| Sucrose | 300.0 grams |
| Dioctyl sodium sulfosuccinate | 0.5 grams |
| Bentonite | 22.5 grams |
| Methyl paraben | 7.5 grams |
| Propyl paraben | 1.5 grams |
| Antifoam A.F. Emulsion | 0.15 grams |
| Propylene Glycol | 52.0 grams |
| FD&C Yellow ≠5 | 0.1 grams |
| Sodium cyclamate | 50.0 grams |
| Sodium saccharin | 5.0 grams |
| Orange Flavor | 7.5 grams |
| Filtered purified water, q.s., ad | 5 liters. |

The parabens were dissolved in the propylene glycol and this solution was added to a solution of the sodium cyclamate, sodium saccharin and sucrose in half the water. The bentonite was suspended in hot (about 85° C.) water and stirred for 60 minutes. The bentonite solution was added to the former solution. The sulfosuccinate was dissolved in some water and the A.I. was suspended in the resulting solution. The Antifoam A.F. Emulsion which was diluted to a lotion consistency with a minimum amount of water was added and mixed well. The latter suspension of A.I. was added to the former mixture and mixed well. Then the FD&C Yellow#5 dissolved in a small amount of water was added, followed by the addition of orange flavor and q.s. to volume with water. The whole was stirred to a homogeneous mixture. The mixture was passed through a colloid mill and filled into suitable containers.

In view of the pharmaceutical activity of the subject compounds, it is evident that the present invention provides a method of ameliorating the blood perfusion of the muscular tissues of the heart and also a method of protecting the heart from myocardial injury caused by more or less brief episodes of ischaemia, anoxia or hypoxia, by the systemic administration of an effective amount of a compound of formula (I), its pharmaceutically acceptable acid addition salt or a stereochemically isomeric form thereof in admixture with a pharmaceutical carrier.

The following examples are intended to illustrate but not to limit the scope of the present invention. Unless otherwise stated all parts therein are by weight.

EXAMPLES

A. Preparation of Intermediates.

Example I

A mixture of 20 parts of 2-chloroethanol, 3 parts of sulfuric acid and 16 parts of benzene was heated on a water-bath. Then there were added dropwise 35 parts of 4-fluoro-α-(4-fluorophenyl)benzenemethanol dissolved in 32 parts of benzene. After the addition was complete, the whole was stirred and refluxed for 4 hours. After cooling the reaction mixture was poured into water. The benzene layer was separated, dried over calcium chloride and evaporated. The residue was distilled in vacuo, yielding 35 parts of 1,1′-[(2-chloroethoxy)methylene]bis[4-fluorobenzene]; bp. 164°–166° C. at 1.5 mm. pressure; $n_D^{20}$: 1.5462; $d_{20}^{20}$: 1.2290 (intermediate 1).

Example II

Through a stirred mixture of 11.7 parts of (5-fluoro-2-hydroxyphenyl)(4-fluorophenyl)methanone and 45 parts of N,N-dimethylformamide nitrogen was bubbled while cooling at about 5° C. (ice-bath). Then there were added portionwise 2.4 parts of sodium hydride dispersion 50%: heavy foaming occurred. Upon completion, there were added 23.6 parts of 1-bromo-3-chloropropane while still cooling at 5° C. The whole was heated to 40° C. and stirring at this temperature was continued for one hour. After cooling to 5° C., the reaction mixture was poured onto 400 parts of water and the product was extracted twice with 180 parts of benzene. The extract was dried, filtered and evaporated. The residue was purified by column-chromatography over silica gel using trichloromethane as eluent. The pure fractions were collected and the eluent was evaporated. The residue solidified on triturating in petroleumether. After cooling to 0° C., the product was filtered off and dried, yielding 10.7 parts (69%) of [2-(3-chloropropoxy)-5-fluorophenyl](4-fluorophenyl)methanone; m.p. 60° C. (intermediate 2).

Example III

A mixture of 16 parts of 1-cyclopropyl-2,2-diphenylethanone and 300 parts of hydrochloric acid were stirred and refluxed for 4 hours. The reaction mixture was cooled and extracted with 2,2′-oxybispropane. The extract was washed with water and with a diluted sodium hydrogen carbonate solution, dried, filtered and evaporated, yielding 17 parts of 5-chloro-1,1-diphenyl-2-pentanone as a residue. (intermediate 3).

Example IV

To a stirred solution of 21.9 parts of 4-fluoro-α-(4-fluorophenyl)benzenemethanamine in 160 parts of 2-propanone were added 11.66 parts of sodium carbonate. Then there were added dropwise 12.43 parts of 2-chloroacetyl chloride at a temperature below 30° C. (cooling in an ice-bath was necessary). Upon completion, stirring was continued first for one hour at room temperature and further for 2 hours at reflux. After cooling to room temperature, the sodium carbonate was filtered off and washed with 2-propanone. The filtrate was evaporated and the residue was crystallized from 2,2′-oxybispropane, yielding 20.6 parts of N-[bis(4-fluorophenyl)-methyl]-2-chloroacetamide; mp. 127.6° C. (intermediate 4).

Example V

To a stirred solution of 10.6 parts of N-(4-fluorophenyl)-4-methylbenzenesulfonamide in 68 parts of N,N-dimethylformamide were added portionwise 2.1 parts of a sodium hydride dispersion 50%: temp. rises to 35° C. After stirring for 20 minutes, the whole was cooled in an ice-bath (about 15° C.) and 12.6 parts of 1-bromo-3-chloropropane were added quickly. Stirring was continued first for 20 minutes at room temperature, then for 3 hours at 75° C. and further overnight at room temperature. The reaction mixture was poured onto ice-water and the product was extracted with methylbenzene. The extract was washed three times with water, dried, filtered and evaporated. The residue was crystallized from petroleumether. The product was filtered off and recrystallized from 2,2′-oxy bispropane, yielding 11.37 parts (83.2%) of N-(3-chloropropyl)-N-(4-fluorophenyl)-4-methylbenzenesulfonamide (intermediate 5).

Following the same procedure and starting from 4-fluoro-N-(4-fluorophenyl)benzamide there was also prepared:

N-(3-chloropropyl)-4-fluoro-N-(4-fluorophenyl)benzamide as a residue (intermediate 6).

Example VI

To a stirred mixture of 25 parts of 1,3-isobenzofurandione and 108.5 parts of fluorobenzene were added portionwise 50 parts of aluminium chloride. Upon completion, the whole was heated slowly to reflux and stirring was continued for 1.50 hours at reflux temperature. The reaction mixture was cooled and poured onto a mixture of crushed ice and 60 parts of concentrated hydrochloric acid. The product was extracted twice with dichloromethane. The combined extracts were washed with a sodium hydroxide solution 10%. The aqueous phase was separated, washed with 2,2′-oxybispropane and acidified with concentrated hydrochloric acid while cooling. The whole was stirred for one hour at room temperature. The precipitated product was filtered off and dissolved in benzene. The solution was distilled azeotropically to dry. The solid residue was stirred in hexane. The product was filtered off and dried in vacuo at about 50° C., yielding 33.5 parts (80.7%) of 2-(4-fluorobenzoyl)benzoic acid; mp. 129.2° C. (intermediate 7).

To 1190 parts of 1,1′-oxybisethane were added at once 50 parts of lithium aluminium hydride. Then there was added dropwise a solution of 213.7 parts of 2-(4-fluorobenzoyl)benzoic acid in 875 parts of 1,1′-oxybisethane so that the mixture was kept at reflux temperature. Upon completion, stirring was continued first for 30 minutes at room temperature, then for 2 hours at reflux and further overnight at room temperature. The reaction mixture was cooled to 0° C. and there were added dropwise successively 50 parts of water, 50 pats of a 15% sodium hydroxide solution and 150 parts of water all at 0° C. The reaction mixture was filtered over Hyflo and washed thoroughly with 1,1′-oxybisethane. The organic phase was separated washed with water, dried, filtered and evaporated. The residue was crystallized from a mixture of benzene and hexane, yielding 170.4 parts of α-(4-fluorophenyl)-1,2-benzenedimethanol; mp. ±75° C. (intermediate 8).

A mixture of 200 parts of α-(4-fluorophenyl)-1,2-benzenedimethanol and 2295 parts of phosphoric acid 60% was stirred for 3 hours at 100° C. Stirring was continued overnight at room temperature. The reaction mixture was poured onto water and the product was extracted twice with 1,1′-oxybisethane. The combined extracts were washed with water, with a 10% sodium carbonate solution and again with water, dried, filtered and evaporated. The residue was distilled, yielding 57 parts of 1-(4-fluorophenyl)-1,3-dihydroisobenzofuran; bp. 108° C. at 0.2 mm. pressure (intermediate 9).

Example VII

To a stirred and cooled (2-propanone/CO$_2$-bath) amount of 1080 parts of ammonia was added 1 part of iron (III)chloride, followed by the portionwise addition of 7.7 parts of sodium under nitrogen atmosphere. After stirring for 20 minutes, there was added dropwise a solution of 64.5 parts of 1-(4-fluorophenyl)-1,3-dihydroisobenzofuran in 105 parts of 1,1'-oxybisethane while still cooling. Then there was added dropwise a solution of 75 parts of 2-(3-bromopropoxy)tetrahydro-2H-pyran in 37 parts of 1,1-oxybisethane. Upon completion, stirring was continued for 2 hours under nitrogen atmosphere in a 2-propanone/$CO_2$-bath. Without cooling and without nitrogen, there were added dropwise slowly 490 parts of 1,1'-oxybisethane and stirring was continued overnight at room temperature. 225 Parts of a saturate ammonium chloride solution were added dropwise followed by the addition of 200 parts of water. The layers were separated and the aqueous phase was extracted twice with 1,1'-oxybisethane. The combined organic phases were washed with water, dried, filtered and evaporated. The residue was purified by column-chromatography over silica gel using a mixture of trichloromethane and methanol (99.5:0.5 by volume) as eluent. The second fraction was collected and the eluent was evaporated, yielding 39.6 parts of 1-(4-fluorophenyl)-1,3-dihydro-1-[3-(tetrahydro-2H-pyran-2-yloxy)propyl]isobenzofuran as a residue (intermediate 10).

39.6 Parts of 1-(4-fluorophenyl)-1,3-dihydro-1-[3-(tetrahydro-2H-pyran-2-yloxy)propyl]isobenzofuran were dissolved in 9.8 parts of a hydrochloric acid solution 0.1M and 788 parts of ethanol and the whole was stirred and refluxed for one hour. The solvent was evaporated and the residue was taken up in methylbenzene and water. The organic phase was separated, washed with water, dried, filtered and evaporated. The residue was purified by column-chromatography over silica gel using a mixture trichloromethane and methanol (99:1 by volume) as eluent. The pure fractions were collected and the eluent was evaporated, yielding 24.2 parts of 1-(4-fluorophenyl)-1,3-dihydroisobenzofuran-1-propanol as a residue (intermediate 11).

To a stirred solution of 24.2 parts of 1-(4-fluorophenyl)-1,3-dihydroisobenzofuran-1-propanol in 8 parts of pyridine and 90 parts of trichloromethane were added dropwise 12.1 parts of thionyl chloride. Upon completion, the whole was heated slowly to 50° C. and stirring at this temperature was continued for 3 hours. The reaction mixture was poured onto ice-water. The organic phase was separated, washed with a sodium hydrogen carbonate solution (10%), dried and evaporated, yielding 20 parts of 1-(3-chloropropyl)-1-(4-fluorophenyl)-1,3-dihydroisobenzofuran as a residue (intermediate 12).

Example VIII

70 Parts of 4-fluorobenzeneacetonitrile were heated at 120° C. and there were added dropwise 83 parts of bromine and stirring was continued for 30 minutes. The resulting reaction mixture was added dropwise to a stirred mixture (room temperature) of 85 parts of aluminium chloride and 200 parts of fluorobenzene (exothermic reaction: temperature rises to 50° C.). After stirring for 30 minutes at 50° C., the reaction mixture was poured onto a mixture of crushed ice and 75 parts of hydrochloric acid solution. The product was extracted with methylbenzene. The extract was dried and evaporated. The residue was crystallized twice from 2-propanol, yielding 51 parts of 4-fluoro-α-(4-fluorophenyl)benzeneacetonitrile, mp. 63.5° C. (intermediate 13).

To a stirred and cooled (ice-bath) mixture of 22.9 parts of 4-fluoro-α-(4-fluorophenyl)benzeneacetonitrile, 23.6 parts of 1-bromo-3-chloropropane and 0.4 parts of N,N,N-triethylbenzenemethanaminium chloride were added dropwise 600 parts of sodium hydroxide solution 50% at a temperature below 30° C. Upon completion, stirring was continued for 3 hours at 50°-60° C. Methylbenzene and water were added and the layers were separated. The organic phase was dried, filtered and evaporated. The residue was evaporated once more in vacuo for 30 minutes at 100° C. to remove the last traces of 1-bromo-3-chloropropane, yielding 29 parts (95%) of α-(3-chloropropyl)-4-fluoro-α-(4-fluorophenyl)benzeneacetonitrile as a residue (intermediate 14).

A mixture of 3 parts of α-(3-chloropropyl)-4-fluoro-α-(4-fluorophenyl)benzeneacetonitrile, 92 parts of concentrated sulfuric acid, 50 parts of water and 50 parts of acetic acid was stirred and refluxed for 24 hours. The reaction mixture was concentrated to about 100 parts and the product was extracted with methylbenzene. The extract was washed with water, dried, filtered and evaporated. The residue was suspended in petroleumether. The product was filtered off and crystalized from 2,2'-oxybispropane, yielding 1.41 parts of 3,3-bis(4-fluorophenyl)tetrahydro-2H-pyran-2-one; mp. 122.4° C. (intermediate 15).

A mixture of 5.8 parts of 3,3-bis(4-fluorophenyl)tetrahydro-2H-pyran-2-one and 30 parts of a solution of hydrobromic acid in glacial acetic acid was stirred over week-end at room temperature. The reaction mixture was poured onto water. The precipitated product was filtered off and dissolved in 2,2'-oxybispropane. The organic phase was washed with water, dried, filtered and evaporated. The residue was boiled in a mixture of 42 parts of 2,2'-oxybispropane and 42 parts of petroleumether. The product was filtered off and crystalized from 2,2'-oxybispropane, yielding 1.27 parts of α-(3-bromopropyl)-4-fluoro-α-(4-fluorophenyl)benzeneacetic acid; mp. 161° C. (intermediate 16).

To a stirred solution of 29.5 parts of α-(3-bromopropyl)-4-fluoro-α-(4-fluorophenyl)benzeneacetic acid in 300 parts of trichloromethane were added 28.8 parts of thionyl chloride and the whole was stirred and refluxed for 3 hours. The reaction mixture was evaporated, yielding 30 parts of α-(3-bromopropyl)-4-fluoro-α-(4-fluorophenyl)benzeneacetyl chloride as a residue (intermediate 17).

A mixture of 30 parts of α-(3-bromopropyl)-4-fluoro-α-(4-fluorophenyl)benzeneacetyl chloride, 9.3 parts of ethanol and 90 parts of methylbenzene was stirred overnight at room temperature. The reaction mixture was evaporated, the residue was taken up in ethanol and the latter was evaporated again. The residue was taken up in 2,2'-oxybispropane. The whole was washed with a saturate sodium hydrogen carbonate solution and with water, dried, filtered and evaporated. The residue was purified by column-chromatography over silica gel using a mixture of trichloromethane and hexane (50:50 by volume) as eluent. The pure fractions were collected and the eluent was evaporated, yielding 19.6 parts of ethyl α-(3-bromopropyl)-4-fluoro-α-(4-fluorophenyl)benzeneacetate as a residue (intermediate 18).

Example IX

To a stirred and cooled (ice-bath) mixture of 50 parts of fluorobenzene and 4.1 parts of 4-(4-fluorophenyl)-4-hydroxycyclohexanone were added portionwise 11 parts of aluminium chloride. Upon completion, stirring was continued for 2 hours while still cooling. The reaction mixture was decomposed by pouring onto a mixture of crushed ice and a hydrochloric acid solution. The product was extracted with methylbenzene. The extract was washed with water till neutralization, dried, filtered and evaporated. The residue was purified by column-chromatography over silica gel using trichloromethane as eluent. The pure fractions were collected and the eluent was evaporated, yielding 4.3 parts (75.9%) of 4,4-bis(4-fluorophenyl)-1-cyclohexanone as a residue (intermediate 19).

Example X

A mixture of 10 parts of bis(fluorophenyl)methanone, 22.1 parts of 3-chloro-1,2-propanediol, 0.2 parts of 4-methylbenzenesulfonic acid hydrate and 90 parts of methylbenzene was stirred and refluxed for 23 hours using a water-separator. The reaction mixture was poured onto alkaline water. Upon stirring, the layers were separated. The organic phase was washed with alkaline water, dried, filtered and evaporated, yielding 14 parts (100%) of 2,2-bis(4-fluorophenyl)-4-(chloromethyl)-1,3-dioxolane as a residue (intermediate 20).

Example XI

To a stirred suspension of 112 parts of 2,3-dibromobutanamide in 880 parts of acetonitrile were added 91 parts of N,N-diethylethanamine and the whole was stirred for 4 hours at room temperature. The formed precipitate was filtered off. To the filtrate were added 112 parts of N,N'-bis(phenylmethyl)-1,2-ethanediamine and 45.5 parts of N,N-diethylethanamine and stirring was continued for 2.50 hours at room temperature. The whole was further stirred for 36 hours at reflux temperature. The reaction mixture was cooled and filtered. The filtrate was evaporated in vacuo. The residue was heated in 675 parts of methylbenzene. The mixture was filtered and the filtrate was evaporated. The oily residue was purified by column-chromatography over silica gel using a mixture of trichloromethane and methanol (95:5 by volume) as eluent. The pure fractions were collected and the eluent was evaporated. The residue was crystallized from 2-propanol, yielding 11 parts of 1,4-bis(phenylmethyl)-2-piperazineacetamide; mp. 113.8° C. (intermediate 21).

Example XII

A mixture of 55.2 parts of methyl 2-pyrazinecarboxylate, 48.9 parts of 2-aminoethanol and 360 parts of ethyl acetate was allowed to stand overnight at room temperature. The precipitated product was filtered off, washed with ethyl acetate and dried, yielding 54.5 parts (80%) of N-(2-hydroxyethyl)-2-pyrazinecarboxamide; mp. 125° C. (intermediate 22).

Example XIII

A mixture of 53.7 parts of N-(2-hydroxyethyl)-2-pyrazinecarboxamide, 20 parts of calcium oxide and 500 parts of 2-methoxyethanol was hydrogenated at normal pressure and at room temperature with 5 parts of palladium-on-charcoal catalyst 10%. After the calculated amount of hydrogen was taken up, the catalyst was filtered off and the filtrate was evaporated, yielding 55.4 parts (100%) of N-(2-hydroxyethyl)-2-piperazinecarboxamide as a residue (intermediate 23).

Following the same hydrogenation procedure there were also prepared:

N,N-dimethyl-2-piperazinecarboxamide as an oily residue (intermediate 24);

N-methyl-2-piperazinecarboxamide as a residue (intermediate 25);

N-(1-methylethyl)-2-piperazinecarboxamide as a residue (intermediate 26); and trans-3-methyl-2-piperazinecarboxamide; mp. 165° C. (intermediate 27).

Example XIV

To a stirred mixture of 60.5 parts of α-methyl-1,4-bis(phenylmethyl)-2-piperazinemethanol and 180 parts of N,N-dimethylformamide were added portionwise 29.8 parts of a sodium hydride dispersion 50% at a temperature below 35° C. under nitrogen atmosphere. The mixture was allowed to cool and stirred for 3 hours at room temperature. After cooling to 10° C., there were added dropwise 9.4 parts of iodomethane at about 20° C. Upon completion, stirring was continued for 2 hours at room temperature. The reaction mixture was poured onto water and the product was extracted twice with 1,1'-oxybisethane. The combined extracts were washed with water, dried, filtered and evaporated, yielding 45.2 parts (71.5%) of 2-(1-methoxyethyl)-1,4-bis(phenylmethyl)piperazine as a residue (intermediate 28).

Following the same procedure, and using iodomethane, respectively, bromoethane as an alkylating agent, there were also prepared:

2-(methoxymethyl)-1,4-bis(phenylmethyl)piperazine as a residue (intermediate 29); and 2-(ethoxymethyl)-1,4-bis(phenylmethyl)piperazine as a residue (intermediate 30).

Example XV

A mixture of 117 parts of 2-(methoxymethyl)-1,4-bis(phenylmethyl)piperazine and 400 parts of methanol was hydrogenated at normal pressure and at room temperature with 5 parts of palladium-on-charcoal catalyst 10%. After the calculated amount of hydrogen was taken up, the catalyst was filtered off and the filtrate was evaporated. The residue was distilled, yielding 38.6 parts (78.8%) of 2-(methoxymethyl)piperazine; bp. 75°-80° C. (intermediate 31).

Following the same hydrogenation procedure there were also prepared:

2-(ethoxymethyl)piperazine as a residue (intermediate 32);

α-methyl-2-piperazinemethanol (intermediate 33);

2-piperazineacetamide; mp. 152° C. (intermediate 34); and 2-(1-methoxyethyl)piperazine as a residue (intermediate 35).

Example XVI

To 1 part of a solution of 2 parts of thiophene in 40 parts of ethanol were added 2.2 parts of benzaldehyde, 2.6 parts of 2-piperazinecarboxamide and 120 parts of methanol. The whole was hydrogenated at normal pressure and at room temperature with 2 parts of platinum-on-charcoal catalyst 5%. After the calculated amount of hydrogen was taken up, the catalyst was filtered off and the filtrate was evaporated. The solid residue was boiled in 64 parts of acetonitrile. The mixture was filtered and the filtrate was allowed to crystallize at room temperature. The product was filtered off and dried, yielding 2.4 parts (55%) of 4-(phenylmethyl)-2-piperazinecarboxamide; mp. 168.3° C. (intermediate 36).

Following the same reductive amination procedure there were also prepared:

4-(phenylmethyl)-2-piperazinemethanol (E)-2-butenedioate (1:2); mp. 189.8° C. (intermediate 37);

3-(methoxymethyl)-1-(phenylmethyl)piperazine as a residue (intermediate 38);

N,N-dimethyl-4-(phenylmethyl)-2-piperazinecarboxamide as a residue (intermediate 39);

3-(ethoxymethyl)-1-(phenylmethyl)piperazine as a residue (intermediate 40);

α-methyl-4-(phenylmethyl)-2-piperazinemethanol; mp. 100.3° C. (intermediate 41);

4-(phenylmethyl)-2-piperazineacetamide; mp. 110.1° C. (intermediate 42);

(A)-3-(1-methoxyethyl)-1-(phenylmethyl)piperazine as a residue (intermediate 43);

(B)-3-(1-methoxyethyl)-1-(phenylmethyl)piperazine as a residue (intermediate 44); and ethyl 4-(phenylmethyl)-2-piperazinecarboxylate as a residue (intermediate 45).

Example XVII

A mixture of 13.2 parts of 4-(phenylmethyl)-2-piperazinecarboxamide, 18.5 parts of 1,1'-(4-chlorobutylidene)bis[4-fluorobenzene], 14.8 parts of sodium carbonate, 0.1 parts of potassium iodide and 200 parts of 4-methyl-2-pentanone was stirred and refluxed for 72 hours using a water-separator. The reaction mixture was cooled to room temperature, filtered and the filtrate was evaporated. The oily residue was purified by column-chromatography over silica gel using a mixture of trichloromethane and methanol (97:3 by volume) as eluent. The pure fractions were collected and the eluent was evaporated. The residue was crystallized from 2,2'-oxybispropane. The product was filtered off and dried, yielding 17.7 parts (63.6%) of 1-[4,4-bis(4-fluorophenyl)butyl]-4-(phenylmethyl)-2-piperazinecarboxamide; mp. 79.2° C. (intermediate 46).

Following the same N-alkylation procedure there were also prepared:

1-[4,4-bis(4-fluorophenyl)butyl]-4-(phenylmethyl)-2-piperazinemethanol ethanedioate (1:2); mp. 158.4° C. (intermediate 47);

ethyl 4-(diphenylmethyl)-2-piperazinecarboxylate; mp. 95.1° C. (intermediate 48);

4-(3-phenyl-2-propenyl)-2-piperazinecarboxamide; mp. 149.6° C. (intermediate 49);

1-[4,4-bis(4-fluorophenyl)butyl]-N,N-dimethyl-4-(phenylmethyl)-2-piperazinecarboxamide as a residue (intermediate 50);

1-[4,4-bis(4-fluorophenyl)butyl]-2-(methoxymethyl)-4-(phenylmethyl)piperazine as a residue (intermediate 51); and ethyl 1-[4,4-bis(4-fluorophenyl)butyl]-4-(phenylmethyl)-2-piperazinecarboxylate as a residue (intermediate 52).

Example XVIII

A mixture of 14.8 parts of 1-[4,4-bis(4-fluorophenyl)butyl]-4-(phenylmethyl)-2-piperazinecarboxamide and 200 parts of methanol was hydrogenated at normal pressure and at room temperature with 2 parts of palladium-on-charcoal catalyst 10%. After the calculated amount of hydrogen was taken up, the catalyst was filtered off and the filtrate was evaporated. The residue was purified by column-chromatography over silica gel using a mixture of trichloromethane and methanol (85:15 by volume) as eluent. The pure fractions were collected and the eluent was evaporated. The residue was crystallized from 2,2'-oxybispropane, yielding 7.9 parts (66.4%) of 1-[4,4-bis(4-fluorophenyl)butyl]-2-piperazinecarboxamide; m.p. 113.6° C. (intermediate 53).

Following the same hydrogenation procedure and starting from the corresponding phenylmethyl derivatives there were also prepared:

1-[4,4-bis(4-fluorophenyl)butyl]-2-piperazinemethanol (intermediate 54);

1-[4,4-bis(4-fluorophenyl)butyl]-N,N-dimethyl-2-piperazinecarboxamide as an oily residue (intermediate 55);

1-[4,4-bis(4-fluorophenyl)butyl]-2-(methoxymethyl)-piperazine as a residue (intermediate 56); and ethyl 1-[4,4-bis(4-fluorophenyl)butyl]-2-piperazinecarboxylate as a residue (intermediate 57).

Example XIX

To a stirred and cooled (10° C.) solution of 7.8 parts of 3-(methoxymethyl)-1-(phenylmethyl)piperazine in 150 parts of trichloromethane were added dropwise during a 10 minutes-period 8.4 parts of trifluoroacetic acid anhydride: exothermic reaction, the temperature rises to 25° C. (cooling with ice-water). Upon completion, stirring was continued for 3 hours at room temperature. The reaction mixture was evaporated. The residue was purified by column-chromatography over silica gel using a mixture of trichloromethane and methanol, saturated with ammonia, (95:5 by volume) as eluent. The first fractions were collected and the eluent was evaporated, yielding 9.2 parts (83%) of 2-(methoxymethyl)-4-(phenylmethyl)-1-(trifluoroacetyl)piperazine as a residue (intermediate 58).

A mixture of 9.2 parts of 2-(methoxymethyl)-4-(phenylmethyl)-1-(trifluoroacetyl)piperazine and 120 parts of methanol was hydrogenated at normal pressure and at room temperature with 2 parts of palladium-on-charcoal catalyst 10%. After the calculated amount of hydrogen was taken up, the catalyst was filtered off and the filtrate was evaporated, yielding 6.05 parts (92%) of 2-(methoxymethyl)-1-(trifluoroacetyl)piperazine as a residue (intermediate 59).

To a stirred mixture of 6.05 parts of 2-(methoxymethyl)-1-(trifluoroacetyl)piperazine, 5.25 parts of N,N-diethylethananamine and 36 parts of N,N-dimethylformamide were added 11 parts of 1,1'-(4-iodobutylidene)-bis[4-fluorobenzene]. Stirring was continued for 4 hours at 75° C. The reaction mixture was cooled and poured onto 400 parts of water. The product was extracted twice with 140 parts of 1,1'-oxybisethane. The combined extracts were dried, filtered and evaporated, yielding 11.5 parts (94%) of 4-[4,4-bis(4-fluorophenyl)-butyl]-2-(methoxymethyl)-1-(trifluoroacetyl)piperazine as a residue (intermediate 60).

A mixture of 11.5 parts of 4-[4,4-bis(4-fluorophenyl)-butyl]-2-(methoxymethyl)-1-(trifluoroacetyl)piperazine and 60 parts of hydrochloric acid solution 6N were stirred and refluxed overnight. The reaction mixture was cooled and washed with 70 parts of 1,1'-oxybisethane. The acidic aqueous phase was alkalized with ammonium hydroxide. The product was extracted twice with 70 parts of 1,1'-oxybisethane. The combined extracts were dried, filtered and evaporated, yielding 6.7 parts (72%) of 1-[4,4-bis(4-fluorophenyl)-butyl]-2-(methoxymethyl)piperazine as a residue (intermediate 61).

Example XX

To a stirred and cooled (about 10° C.) solution of 11.7 parts of 2-methoxy-5-(trifluoromethyl)benzenamine in 50 parts of acetic acid were added dropwise 7.7 parts of chloroacetyl chloride at a temperature below 20° C. After stirring for 30 minutes, there was added dropwise a solution of 24.8 parts of sodium acetate in 62 parts of water (exothermic reaction). Upon completion, stirring was continued for 30 minutes at room temperature. The precipitated product was filtered off, washed with a lot of water and dried, yielding 15.5 parts (93.3%) of 2-chloro-N-[2-methoxy-5-(trifluoromethyl)phenyl]-acetamide; mp. 94.7° C. (intermediate 62).

In a similar manner there were also prepared:
3-chloro-N-(2,6-dichlorophenyl)propanamide; mp. 143° C. (intermediate 63);
2-chloro-N-(5-fluoro-2-methylphenyl)acetamide; mp. 110.1° C. (intermediate 64); and
2-chloro-N-(5-chloro-2-methylphenyl)acetamide; mp. 138.5° C. (intermediate 65).

Example XXI

To a stirred solution of 49.2 parts of 2-methoxy-5-methylbenzenamine and 270 parts of methylbenzene were added dropwise 22.5 parts of 2-chloroacetyl chloride while cooling (ice-bath) at 10°-20° C. Upon completion, stirring was continued for 1.50 hours at room temperature. 200 Parts of water were added. The organic phase was separated, washed with water, dried, filtered and evaporated. The oily residue was crystallized from 2,2'-oxybispropane. The product was filtered off and dried, yielding 28.2 parts (66%) of 2-chloro-N-(2-methoxy-5-methylphenyl)acetamide; mp. 83.9° C. (intermediate 66).

In a similar manner there were also prepared:
2-chloro-N-(2,6-dichloro-4-cyanophenyl)acetamide(intermediate 67);
N-(4-acetyl-2,6-dichlorophenyl)-2-chloroacetamide (intermediate 68); and
2-chloro-N-(5-chloro-2-methoxy-4-nitrophenyl)acetamide; mp. 130.9° C. (intermediate 69).

Example XXII

To 1 part of a solution of 2 parts of thiophene in 40 parts of ethanol were added 15 parts of 2-chloro-N-(2-methyl-4-nitrophenyl)acetamide and 400 parts of methanol. The whole was hydrogenated at normal pressure and at room temperature with 2 parts of platinum-on-charcoal catalyst 5%. After the calculated amount of hydrogen was taken up, the catalyst was filtered off and the filtrate was evaporated. The solid residue was purified by column-chromatography over silica gel using a mixture of trichloromethane and methanol (95:5 by volume) as eluent. The pure fractions were collected and the eluent was evaporated. The residue was suspended in 2,2'-oxybispropane. The product was filtered off and dried, yielding 12 parts (92%)of N-(4-amino-2-methylphenyl)-2-chloroacetamide (intermediate 70).

Example XXIII 16.8 Parts of concentrated sulfuric acid were stirred and cooled to 0° C. and there were added portionwise 4.2 parts of 2-chloro-N-(2,6-dichloro-4-cyanophenyl)acetamide. Upon completion, stirring was continued for 3 hours in an ice-bath. The reaction mixture was allowed to stand overnight at room temperature and poured onto ice-water. The precipitated product was filtered off, washed with water, dried and boiled in acetonitrile. The product was filtered off and dried, yielding 2.7 parts of 3,5-dichloro-4-[(2-chloroacetyl)amino]benzamide; mp. +260° C. (intermediate 71).

Example XXIV

A mixture of 12.8 parts of $N^1$-(2,6-dimethylphenyl)-4-(phenylmethyl)-1,2-piperazinediacetamide and 120 parts of methanol was hydrogenated at normal pressure and at room temperature with 2 parts of palladium-on-charcoal catalyst 10%. After the calculated amount of hydrogen was taken up, the catalyst was filtered off and the filtrate was evaporated. The oily residue was crystallized from acetonitrile, yielding 7.7 parts (97.5%) of $N^1$-(2,6-dimethylphenyl)-1,2-piperazinediacetamide; mp. 171.9° C. (intermediate 72).

Following the same hydrogenation procedure and starting from the corresponding phenylmethyl derivatives there were also prepared:
N-(2,6-dimethylphenyl)-2-(hydroxymethyl)-1-piperazineacetamide; mp. 134.1° C. (intermediate 73);
2-(aminocarbonyl)-N-(2,6-dimethylphenyl)-1-piperazineacetamide as a solid residue (intermediate 74);
ethyl 1-[2-[(2,6-dimethylphenyl)amino]-2-oxoethyl]-2-piperazinecarboxylate as a residue (intermediate 75);
N-(2,6-dimethylphenyl)-2-(methoxymethyl)-1-piperazineacetamide as a residue (intermediate 76);
2-(dimethylaminocarbonyl)-N-(2,6-dimethylphenyl)-1-piperazineacetamide as a residue (intermediate 77);
(A+B)-N-(2,6-dimethylphenyl)-2-(ethoxymethyl)-α-methyl-1-piperazineacetamide as a residue (intermediate 78);
N-(2,6-dimethylphenyl)-2-(ethoxymethyl)-1-piperazineacetamide as a residue (intermediate 79);
N-(2,6-dimethylphenyl)-2-(1-hydroxyethyl)-1-piperazineacetamide; mp. 151.9° C. (intermediate 80);
(B)-N-(2,6-dimethylphenyl)-2-(1-methoxyethyl)-1-piperazineacetamide as a residue (intermediate 81); and
(A)-N-(2,6-dimethylphenyl)-2-(1-methoxyethyl)-1-piperazineacetamide as a residue (intermediate 82).

Example XXV

To a stirred and warm solution of 3 parts of 2-piperazinecarboxamide in 16 parts of 2-methoxyethanol were added 51.2 parts of 2-propanone. The whole was stirred and refluxed for 20 hours. The reaction mixture was evaporated. The solid residue was crystallized from acetonitrile, yielding 2.5 parts (64%) of hexahydro-3,3-dimethylimidazo[1,5-a]pyrazin-1(5H)-one; mp. 174.2° C. (intermediate 83).

In a similar manner there were also prepared:
hexahydro-2,3,3-trimethylimidazo[1,5-a]pyrazin-1(5H)-one as a residue (intermediate 84);
hexahydro-2-(2-hydroxyethyl)-3,3-dimethylimidazo[1,5-a]pyrazin-1(5H)-one; mp. 95° C. (intermediate 85);
hexahydro-3,3-dimethyl-2-(1-methylethyl)imidazo[1,5-a]pyrazin-1(5H)-one (intermediate 86);
hexahydro-3,3,8-trimethylimidazo[1,5-a]pyrazin-1(2H)-one (intermediate 87); and
N-(2,6-dichlorophenyl)hexahydro-3-methyl-(2-methylpropyl)-1-oxoimidazo[1,5-a]pyrazine-7(8H)-acetamide; mp. 227.3° C. (intermediate 88).

Example XXVI

To a stirred solution of 45 parts of 2-piperazinemethanol in 211 parts of warm 2-methoxyethanol were added 675 parts of 2-propanone and stirring was continued for 27 hours at reflux temperature. The reaction mixture was allowed to cool to room temperature over week-end. The solvent was evaporated and the residue was taken up in methylbenzene. The mixture was filtered yielding. 41.4 parts of hexahydro-3,3-dimethyl-3H-oxazolo[3,4-a]pyrazine. (intermediate 89).

Example XXVII

A mixture of 169.8 parts of 1,1'-(4-chlorobutylidene)-bis[4-fluorobenzene], 93.5 parts of hexahydro-3,3-dimethylimidazo[1,5-a]pyrazin-1(5H)-one, 128.3 parts of sodium carbonate, 0.1 parts of potassium iodide and 1200 parts of 4-methyl-2-pentanone was stirred and refluxed for 8 hours using a water-separator. After cooling overnight to room temperature, the reaction mixture was filtered. The filtrate was evaporated. The residue was purified by column-chromatography over silica gel using a mixture of trichloromethane and methanol (95:5 by volume) as eluent. The pure fractions were collected and the eluent was evaporated. The residue was triturated in 2,2'-oxybispropane. The product was filtered off and dried, yielding 108 parts of 7-[4,4-bis(4-fluorophenyl)butyl]hexahydro-3,3-dimethylimidazo[1,5-a]pyrazin-1(5H)-one; mp. 148.4° C. (intermediate 90).

Following the same N-alkylation procedure, and using equivalent amounts of the appropriate starting materials, there were also prepared:

7-[4,4-bis(4-fluorophenyl)butyl]hexahydro-2,3,3-trimethylimidazo[1,5-a]pyrazin-1(5H)-one monohydrochloride (intermediate 91);

7-[4,4-bis(4-fluorophenyl)butyl]hexahydro-2-(2-hydroxyethyl)-3,3-dimethylimidazo[1,5-a]pyrazin-1(5H)-one as a residue (intermediate 92); and 7-[4,4-bis(4-fluorophenyl)butyl]hexahydro-3,3-dimethyl-2-(1-methylethyl)imidazo[1,5-a]pyrazin-1(5H)-one as a residue (intermediate 93).

Example XXVIII

A mixture of 30.7 parts of 1,1'-(4-iodobutylidene)-bis[4-fluorobenzene], 11.5 parts of hexahydro-3,3-dimethyl-1H-oxazolo-[3,4-a]pyrazine, 14.8 parts of sodium carbonate and 270 parts of N,N-dimethylformamide was stirred for 5 hours at about 70° C. The reaction mixture was cooled overnight to room temperature and the solvent was evaporated. The residue was dissolved in trichloromethane. The organic phase was washed with water, dried, filtered and evaporated, yielding 34 parts of 7-[4,4-bis(4-fluorophenyl)butyl]hexahydro-3,3-dimethyl-1H-oxazolo[3,4-a]pyrazine as a residue (intermediate 94).

Example XXIX

A mixture of 40 parts of 7-[4,4-bis(4-fluorophenyl)butyl]hexahydro-2-(2-hydroxyethyl)-3,3-dimethylimidazo[1,5-a]pyrazin-1(5H)-one, 19 parts of hydrochloric acid solution 10.5N and 400 parts of water was stirred for one hour in a boiling water-bath on a Rotavapor. After cooling, the reaction mixture was washed twice with 140 parts of 1,1'-oxybisethane. The aqueous phase was alkalized with ammonium hydroxide. The product was extracted twice with 140 parts of 1,1'-oxybisethane. The combined extracts were dried, filtered and evaporated. The residue was purified by column-chromatography over silica gel using first a mixture of trichloromethane and methanol (90:10 by volume) and then a mixture of trichloromethane and methanol saturated with ammonia (90:10 by volume) as eluents. The pure fractions were collected and the eluent was evaporated, yielding 33.7 parts (100%) of 4-[4,4-bis(4-fluorophenyl)butyl]-N-(2-hydroxyethyl)-2-piperazinecarboxamide (intermediate 95).

In a similar manner there were also prepared:

4-[4,4-bis(4-fluorophenyl)butyl]-N-methyl-2-piperazinecarboxamide as a residue (intermediate 96);

4-[4,4-bis(4-fluorophenyl)butyl]-2-piperazinecarboxamide as an oily residue (intermediate 97);

4-[4,4-bis(4-fluorophenyl)butyl]-N-(1-methylethyl)-2-piperazinecarboxamide (intermediate 98); and trans-3-(aminocarbonyl)-N-(2,6-dichlorophenyl)-2-methyl-1-piperazineacetamide; mp. 254.6° C. (intermediate 99).

Example XXX

A mixture of 34 parts of 7-[4,4-bis(4-fluorophenyl)butyl]hexahydro-3,3-dimethyl-1H-oxazolo[3,4-a]pyrazine and 272 parts of a hydrochloric acid solution 0.5N in water was stirred and refluxed for 2 hours. The reaction mixture was cooled to room temperature and the product was extracted twice with 1,1'-oxybisethane. The aqueous phase was separated, alkalized and salted out with sodium carbonate. The product was extracted with trichloromethane. The extract was dried, filtered and evaporated. The residue was purified by column-chromatography over silica gel using a mixture of trichloromethane and methanol (85:15 by volume), saturated with ammonia as eluent. The pure fractions were collected and the eluent was evaporated, yielding 17.0 parts of 4-[4,4-bis(4-fluorophenyl)butyl]-2-piperazinemethanol as an oily residue (intermediate 100).

Example XXXI

A mixture of 8.2 parts of 2-chloro-N-(2,6-dimethylphenyl)acetamide, 7.2 parts of hexahydro-3,3-dimethyl-2-(1-methylethyl)imidazo[1,5-a]pyrazin-1(5H)-one, 7 parts of N,N-diethylethanamine and 54 parts of N,N-dimethylformamide was stirred and heated for 3 hours at 75° C. After cooling to 0° C., the precipitate was filtered off and the filtrate was evaporated. The residue was dissolved in 300 parts of trichloromethane. This solution was washed with 50 parts of water, dried, filtered and evaporated. The residue was triturated in 2,2'-oxybispropane. After cooling to 0° C., the product was filtered off and dried, yielding 9.2 parts (72.7%) of N-(2,6-dimethylphenyl)hexahydro-3,3-dimethyl-2-(1-methylethyl)-1-oxoimidazo[1,5-a]pyrazine-7(8H)-acetamide; mp. 155° C. (intermediate 101).

Following the same N-alkylation procedure, and using equivalent amounts of the appropriate starting materials, there were also prepared:

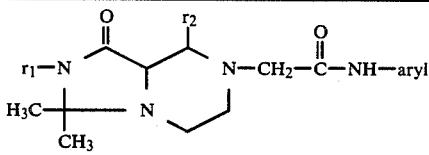

| Intermediate | r₁ | r₂ | aryl | mp. °C. |
|---|---|---|---|---|
| 102 | CH₃ | H | 2,6-(CH₃)₂—C₆H₃— | 180 |
| 103 | H | H | 2,6-(CH₃)₂—C₆H₃— | 194.8 |
| 104 | CH(CH₃)₂ | H | 2,6-Cl₂—C₆H₃— | — |
| 105 | CH₂—CH₂OH | H | 2,6-Cl₂—C₆H₃— | — |
| 106 | CH₃ | H | 2,6-Cl₂—C₆H₃— | 174.6 |
| 107 | CH₃ | H | 2-Cl, 6-CH₃—C₆H₃— | 174.1 |
| 108 | H | H | 2,4,6-(CH₃)₃—C₆H₂— | — |
| 109 | H | H | 2-CH₃, 6-C₂H₅—C₆H₃— | 160.4 |
| 110 | H | H | 2,6-[CH(CH₃)₂]₂—C₆H₃— | oil |
| 111 | CH₃ | H | 2-COCH₃—C₆H₄— | 149.0 |
| 112 | CH₃ | H | 2,4,6-(CH₃)₃—C₆H₂— | 117.6 |
| 113 | H | H | 2-COOCH₃—C₆H₄— | 207.6 |
| 114 | CH₃ | H | 2,6-(CH₃)₂, 4-NO₂—C₆H₂— | 191.9 |
| 115 | H | H | 2,6-Cl₂—C₆H₃— | 207.9 |
| 116 | CH₃ | H | 2-CH₃, 4-NO₂—C₆H₃— | 201.6 |
| 117 | H | H | 2-CONH₂—C₆H₄— | — |
| 118 | CH₃ | H | 2-CH₃, 5-Cl—C₆H₃— | 199.7 |
| 119 | H | CH₃ | 2,6-Cl₂—C₆H₃— | — |
| 120 | H | H | 2-OCH₃—C₆H₄— | 189.8 |

Example XXXII

A mixture of 6.6 parts of 2-chloro-N-(5-fluoro-2-methylphenyl)acetamide, 5 parts of hexahydro-3,3-dimethyl-3H-oxazolo[3,4-a]pyrazine, 6.1 parts of N,N-diethylethanamine and 67.5 parts of N,N-dimethylformamide was stirred and heated for 8 hours at about 70° C. After cooling overnight to room temperature, the reaction mixture was evaporated. The residue was dissolved in trichloromethane. The solution was washed with water, dried, filtered and evaporated, yielding 8.5 parts of N-(5-fluoro-2-methylphenyl)-tetrahydro-3,3-dimethyl-3H-oxazolo[3,4-a]pyrazine-7(8H)-acetamide as an oily residue (intermediate 121).

Following the same N-alkylation procedure and using equivalent amounts of the appropriate starting materials there were also prepared:

N-(2,6-dimethyl-4-nitrophenyl)tetrahydro-3,3-dimethyl-3H-oxazolo[3,4-a]pyrazine-7(8H)-acetamide as an oily residue; (intermediate 122);

N-(2,6-dichlorophenyl)tetrahydro-3,3-dimethyl-3H-oxazolo[3,4-a]pyrazine-7(8H)-acetamide as an oily residue (intermediate 123); and N-(2-chloro-6-methylphenyl)tetrahydro-3,3-dimethyl-3H-oxazolo[3,4-a]pyrazine-7(8H)-acetamide as an oily residue (intermediate 124).

Example XXXIII

A mixture of 23.8 parts of N-(2,6-dichlorophenyl)-hexahydro-3,3-dimethyl-1-oxoimidazo[1,5-a]pyrazine-7(8H)-acetamide and 256 parts of a hydrochloric acid solution 0.5N was stirred and refluxed for 2 hours. The reaction mixture was cooled overnight to room temperature, alkalized and salted out with sodium carbonate. The product was extracted with trichloromethane. The extract was filtered and the filtrate was dried, filtered and evaporated. The residue was crystallized from acetonitrile, yielding 13.6 parts (64%) of 3-(aminocarbonyl)-N-(2,6-dichlorophenyl)-1-piperazineacetamide; mp. 180.4°-182.8° C. (intermediate 125).

Following the same hydrolysis procedure, and starting from the corresponding imidazo[1,5-a]pyrazine, there were also prepared:

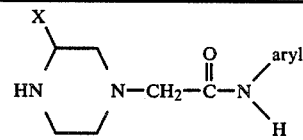

| Intermediate | X | aryl | mp. °C. |
|---|---|---|---|
| 126 | CO—NHCH₃ | 2,6-(CH₃)₂—C₆H₃— | — |
| 127 | CO—NH₂ | 2,6-(CH₃)₂—C₆H₃— | 190.1 |
| 128 | CO—NHCH(CH₃)₂ | 2,6-(CH₃)₂—C₆H₃— | — |
| 129 | CO—NHCH(CH₃)₂ | 2,6-Cl₂—C₆H₃— | — |
| 130 | CO—NHCH₂CH₂OH | 2,6-Cl₂—C₆H₃— | — |
| 131 | CO—NHCH₃ | 2,6-Cl₂—C₆H₃— | 167.6 |
| 132 | CO—NH₂ | 2,4,6-(CH₃)₃—C₆H₂— | — |
| 133 | CO—NH₂ | 2,6-[CH(CH₃)₂]₂—C₆H₃— | — |
| 134 | CO—NHCH₃ | 2-Cl—6-CH₃—C₆H₃— | 146.2 |
| 135 | CO—NH₂ | 2-CH₃—6-C₂H₅—C₆H₃— | — |
| 136 | CO—NHCH₃ | 2,6-(CH₃)₂, 4-NO₂—C₆H₂— | 203.2 |
| 137 | CO—NHCH₃ | 2,4,6-(CH₃)₃—C₆H₂— | 202.3 |
| 138 | CO—NH₂ | 2-CONH₂—C₆H₄— | — |
| 139 | CO—NHCH₃ | 2-COCH₃—C₆H₄— | — |
| 140 | CO—NH₂ | 2-COOCH₃—C₆H₄— | — |
| 141 | CO—NHCH₃ | 2-CH₃, 4-NO₂—C₆H₃— | — |
| 142 | CO—NHCH₃ | 5-Cl—2—CH₃-C₆H₃— | 132.6 |
| 143 | CO—NHCH₃ | 2-OCH₃—C₆H₃— | 169.9 |

Example XXXIV

A mixture of 8.5 parts of N-(5-fluoro-2-methylphenyl)tetrahydro-3,3-dimethyl-3H-oxazolo[3,4-a]pyrazine-7(8H)-acetamide and 105.6 parts of hydrochloric acid solution 0.5N was stirred and refluxed for 2 hours. The reaction mixture was cooled to room temperature. The whole was alkalized with sodium carbonate and salted out. The product was extracted with trichloromethane. The extract was washed with water, dried, filtered and evaporated. The residue was purified by column-chromatography over silica gel using a mixture of trichloromethane and methanol, saturated with ammonia (85:15 by volume) as eluent. The pure fractions were collected and the eluent was evaporated. The residue was triturated in 2,2'-oxybispropane. The product was filtered off and dried, yielding 4.4 parts (59.4%) of N-(5-fluoro-2-methylphenyl)-3-(hydroxymethyl)-1-piperazineacetamide; mp. 127.7° C. (intermediate 145).

Following the same hydrolysis procedure, and starting from the corresponding oxazolo[3,4-a]pyrazine, there were also prepared:

N-(2,6-dimethyl-4-nitrophenyl)-3-(hydroxymethyl)-1-piperazineacetamide; mp. 161.8° C. (intermediate 146);

N-(2,6-dichlorophenyl)-3-(hydroxymethyl)-1-piperazineacetamide; mp. 117.2° C. (intermediate 147); and N-(2-chloro-6-methylphenyl)-3-(hydroxymethyl)-1-piperazineacetamide; mp. 116.3° C. (intermediate 148).

B. Preparation of final compounds

Example XXXV

To a stirred mixture of 4.56 parts of N-(2,6-dimethylphenyl)-3-(methylaminocarbonyl)-1-piperazineacetamide, 3.2 parts of sodium carbonate and 36 parts of N,N-dimethylformamide were added 6.7 parts of 1,1'-(4-iodobutylidene)bis[4-fluorobenzene]. Stirring was continued for one hour at 75° C. The reaction mixture was cooled and poured onto 400 parts of water. The precipitated product was filtered off and dissolved in 360 parts of dichloromethane. The solution was washed with 100 parts of water, dried, filtered and evaporated. The residue was converted into the hydrochloride salt in 2-propanol. The whole was evaporated and the oily residue was suspended three times in 1,1'-oxybisethane. The latter was decanted and the residue was allowed to stand for one hour with acetonitrile. The solid precipitate was filtered off, washed with warm acetonitrile and dried, yielding 7.44 parts (79.8%) of 4-[4,4-bis(4-fluorophenyl)butyl]-N-(2,6-dimethylphenyl)-3-(methylaminocarbonyl)-1-piperazineacetamide dihydrochloride; mp. 228.2° C. (compound 1).

Following the same N-alkylation procedure and using equivalent amounts of the appropriate starting materials there were also prepared:

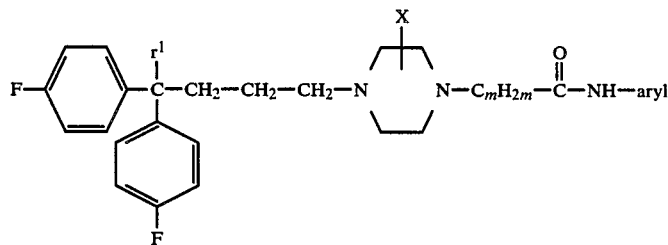

| compound | $r^1$ | X | $C_mH_{2m}$ | aryl | A/B | Salt or base form | mp. °C. |
|---|---|---|---|---|---|---|---|
| 2 | H | 2-CH$_2$OH | CH$_2$ | 2,6-(CH$_3$)$_2$—C$_6$H$_3$— | | (E)—2-butenedioate (2:3) | 149.3 |
| 3 | H | 2-CONH$_2$ | CH$_2$ | 2,6-(CH$_3$)$_2$—C$_6$H$_3$— | | base | 159.9 |
| 4 | H | 2-CH$_2$OCH$_3$ | CH$_2$ | 2,6-(CH$_3$)$_2$—C$_6$H$_3$— | | 2 HCl.H$_2$O | 161.1 |
| 5 | H | 2-CONH$_2$ | CH$_2$ | 2,6-(CH$_3$)$_2$—C$_6$H$_3$— | | 2 HCl.H$_2$O | 220.4 |
| 6 | H | 2-CON(CH$_3$)$_2$ | CH$_2$ | 2,6-(CH$_3$)$_2$—C$_6$H$_3$— | | 2 HCl.H$_2$O | 176.9 |
| 7 | CN | 3-CONH$_2$ | CH$_2$ | 2,6-(CH$_3$)$_2$—C$_6$H$_3$— | | base | 93.9 |
| 8 | CON(CH$_3$)$_2$ | 3-CONH$_2$ | CH$_2$ | 2,6-(CH$_3$)$_2$—C$_6$H$_3$— | | ½ H$_2$O | 105.8 |
| 9 | H | 2-CH$_2$OC$_2$H$_5$ | CH(CH$_3$) | 2,6-(CH$_3$)$_2$—C$_6$H$_3$— | A | 2 HCl.½ H$_2$O | 141.6 |
| 10 | H | 2-CH$_2$OC$_2$H$_5$ | CH$_2$ | 2,6-(CH$_3$)$_2$—C$_6$H$_3$— | | 2 HCl.H$_2$O | 175.5 |
| 11 | CON(CH$_3$)$_2$ | 2-CH$_2$OH | CH$_2$ | 2,6-(CH$_3$)$_2$—C$_6$H$_3$— | | base | 175.4 |
| 12 | H | 2-CH$_2$CONH$_2$ | CH$_2$ | 2,6-(CH$_3$)$_2$—C$_6$H$_3$— | | base | 157.1 |
| 13 | CN | 2-CH$_2$OH | CH$_2$ | 2,6-(CH$_3$)$_2$—C$_6$H$_3$— | | 2 HCl | 166.8 |
| 14 | H | 3-CONHCH(CH$_3$)$_2$ | CH$_2$ | 2,6-(CH$_3$)$_2$—C$_6$H$_3$— | | 2 HCl | 208.9 |
| 15 | H | 3-CONHCH(CH$_3$)$_2$ | CH$_2$ | 2,6-Cl$_2$—C$_6$H$_3$— | | 2 HCl | 206.4 |
| 16 | H | 2-CH(CH$_3$)—OH | CH$_2$ | 2,6-(CH$_3$)$_2$—C$_6$H$_3$— | | 2 HCl.H$_2$O | 150.3 |
| 17 | H | 3-CONHCH$_2$CH$_2$OH | CH$_2$ | 2,6-Cl$_2$—C$_6$H$_3$— | | 2 HCl | 201.2-204 |
| 18 | H | 3-CH$_2$OH | CH$_2$ | 2,6-Cl$_2$—C$_6$H$_3$— | | base | 150.0 |
| 19 | H | 2-CH(CH$_3$)OCH$_3$ | CH$_2$ | 2,6-(CH$_3$)$_2$—C$_6$H$_3$— | B | 2 HCl.H$_2$O | 173.3 |
| 20 | H | 3-CONH$_2$ | CH$_2$ | 2,4,6-(CH$_3$)$_3$—C$_6$H$_2$— | | 2 HCl.H$_2$O | 204.6 |
| 21 | H | 3-CONH$_2$ | CH$_2$ | 2,6-[CH(CH$_3$)$_2$]$_2$—C$_6$H$_3$— | | 2 HCl.H$_2$O | 208.1 |
| 22 | H | 3-CH$_2$OH | CH$_2$ | 2-CH$_3$—5-F—C$_6$H$_3$— | | 2 HCl | 192.9-199.8 |
| 23 | H | 2-CH(CH$_3$)OCH$_3$ | CH$_2$ | 2,6-(CH$_3$)$_2$—C$_6$H$_3$— | A | (COOH)$_2$ | 177.9 |
| 24 | H | 3-CONH$_2$ | CH$_2$ | 2-CH$_3$—6-C$_2$H$_5$—C$_6$H$_3$— | | 2 HCl.H$_2$O | 202.3 |
| 25 | H | 3-CONHCH$_3$ | CH$_2$ | 2,6-(CH$_3$)$_2$—C$_6$H$_3$— | | 2 HCl | 214.6-216.4 |
| 26 | H | 3-CONHCH$_3$ | CH$_2$ | 2,6-Cl$_2$—C$_6$H$_3$— | | 2 HCl | 222.8 |
| 27 | H | 3-CONH$_2$ | CH$_2$ | 2,6-Cl$_2$—C$_6$H$_3$— | | base | 159.2 |
| 28 | H | 3-CONH$_2$ | CH$_2$ | 2-CONH$_2$—C$_6$H$_4$— | | base | 200.8 |
| 29 | H | 3-CONHCH$_3$ | CH$_2$ | 2-COCH$_3$—C$_6$H$_4$— | | base | 70.7 |
| 30 | H | 3-CONHCH$_3$ | CH$_2$ | 2,4,6-(CH$_3$)$_3$—C$_6$H$_2$— | | base | 82.3 |
| 31 | H | 3-CONHCH$_3$ | CH$_2$ | 2-CH$_3$, 5-Cl—C$_6$H$_3$— | | 2 HCl | 190-225 |

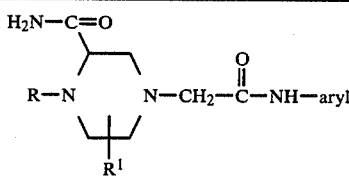

| Compound | R | R¹ | aryl | Isomeric form | Salt or base form | mp. in °C. |
|---|---|---|---|---|---|---|
| 32 | [4-F—2-[(4-F—C6H4)CO]C6H3]—O—(CH2)3— | H | 2,6-(CH3)2—C6H3— | — | HCl | 187.8 |
| 33 | (4-F—C6H4)2CH—NHCO—CH2— | H | 2,6-(CH3)2—C6H3— | — | base | 164.7 |
| 34 | (4-F—C6H4)[(4-CH3—C6H4)SO2]—N—(CH2)3— | H | 2,6-(CH3)2—C6H3— | — | 2 HCl.H2O | 200.6–204.8 |
| 35 | ![structure] | H | 2,6-(CH3)2—C6H3— | — | base | 196.9 |
| 36 | ![structure] | H | 2,6-(CH3)2—C6H3— | A | base | 211.4–214.4 |
| 37 | ![structure] | H | 2,6-(CH3)2—C6H3— | B | base | 99.0 |
| 38 | (4-F—C6H4)CO—(CH2)3— | H | 2,6-Cl2—C6H3— | — | base | 177.1 |
| 39 | (4-F—C6H4)—O—(CH2)3— | H | 2,6-Cl2—C6H3— | — | base | 139.1 |
| 40 | (4-F—C6H4)CH=CH—CH2—CH2— | H | 2,6-Cl2—C6H3— | — | base | 105.1 |
| 41 | (4-F—C6H4)2CH—(CH2)3— | 2-CH3 | 2,6-Cl2—C6H3— | trans | 2HCl.H2O | 213.3 |
| 42 | (4-F—C6H4)[(4-F—C6H4)CO]—N—(CH2)3— | H | 2,6-Cl2—C6H3— | — | 2HCl.2H2O | 182.0–201.5 |
| 43 | (4-F—C6H4)(2-thienyl)CH—(CH2)3— | H | 2,6-Cl2—C6H3— | — | 2HCl | 181.8 |
| 44 | C6H5—NH—CH2—CH2— | H | 2,6-Cl2—C6H3— | — | 2HCl. ½ CH3CH(OH)—CH3.H2O | 169.3 |
| 45 | (4-F—C6H4)CH2—(CH2)3— | H | 2,6-Cl2—C6H3— | — | base | 148.8 |
| 46 | ![structure] | H | 2,6-Cl2—C6H3— | — | 2HCl.H2O | 198.5 |
| 47 | (4-F—C6H4)2CH—(CH2)6— | H | 2,6-Cl2—C6H3— | — | 2HCl.H2O | 195.4 |
| 48 | (4-F—C6H4)(3-pyridinyl)C=CH—(CH2)2— | H | 2,6-Cl2—C6H3— | — | H2O | 98.2 |

Example XXXVI

A mixture of 5 parts of 1,1'-(5-chloropentylidene)-bis(4-fluorobenzene), 5 parts of 3-(aminocarbonyl)-N-(2,6-dichlorophenyl)-1-piperazineacetamide, 2.2 parts of sodium carbonate, 0.1 parts of potassium iodide and 120 parts of 4-methyl-2-pentanone was stirred and refluxed for 24 hours. The reaction mixture was cooled and purified by column-chromatography (2x) over silica gel using first a mixture of trichloromethane and methanol (95:5 by volume) and then a mixture of trichloromethane and methanol (97:3 by volume) as eluents. The pure fractions were collected and the eluent was evaporated. The residue was converted into the hydrochloride salt in acetonitrile and 2-propanol. After stirring for one hour at room temperature, the salt was filtered off and dried, yielding 1.53 parts of 3-(aminocarbonyl)-4-[4,4-bis(4-fluorophenyl)pentyl]-N-(2,6-dichlorophenyl)-1-piperazineacetamide dihydrochloride monohydrate; mp. 206.2° C. (compound 49).

In a similar manner there was also prepared:
3-(aminocarbonyl)-N-(2,6-dichlorophenyl)-4-[2-[bis(4-fluorophenyl)methoxy]ethyl]-1-piperazineacetamide; mp. 185.8° C. (compound 50).

Example XXXVII

A mixture of 7.4 parts of 1,1'-(4-iodobutylidene)bis[4-fluorobenzene], 5.5 parts of N-(2-chloro-6-methylphenyl)-3-(hydroxymethyl)-1-piperazineacetamide, 4.0 parts of N,N-diethylethanamine and 68 parts of N,N-dimethylformamide was stirred for 4 hours at about 70° C. The reaction mixture was cooled overnight to room temperature and the solvent was evaporated. The residue was taken up in trichloromethane. The organic phase was washed with water, dried, filtered and evaporated. The oily residue was purified by column-chromatography over silica gel using a mixture of trichloromethane and methanol (95:5 by volume) as eluent. The pure fractions were collected and the eluent was evaporated. The oily residue solidified on triturating in 2,2'-oxybispropane. The product was filtered off and dried, yielding 3.21 parts (33.1%) of 4-[4,4-bis(4-fluorophenyl)butyl]-N-(2-chloro-6-methylphenyl)-3-(hydroxymethyl)-1-piperazineacetamide; mp. 149.8° C. (compound 51).

Following the same N-alkylation procedure and using equivalent amounts of the appropriate starting materials there were also prepared:

eluent. The pure fractions were collected and the eluent was evaporated. The residue was converted into the hydrochloride salt in 2-propanol and acetonitrile. Upon stirring overnight, the salt was filtered off and dried over week-end, yielding 1.39 parts (23%) of 3-(aminocarbonyl)-N-(2,6-dichlorophenyl)-4-[2-hydroxy-3-(2-naphthalenyloxy)propyl]-1-piperazineacetamide dihydrochloride monohydrate; mp. 155.3° C. (compound 69).

In a similar manner there was also prepared:
3-(aminocarbonyl)-4-[4,4-bis(4-fluorophenyl)-2-hydroxybutyl]-N-(2,6-dimethylphenyl)-1-piperazineacetamide; mp. 110.2° C. (compound 70).

Example XXXIX

A mixture of 4.3 parts of 4,4-bis(4-fluorophenyl)cyclohexanone, 4.35 parts of 3-(aminocarbonyl)-N-(2,6-dimethylphenyl)-1-piperazineacetamide, 1 part of a solution of thiophene in ethanol 4% and 150 parts of 2-methoxyethanol was hydrogenated at normal pressure and at room temperature with 2 parts of palladium-on-charcoal catalyst 10%. After the calculated amount of hydrogen was taken up, the catalyst was filtered off and the filtrate was evaporated. The residue was purified by column-chromatography over silica gel using a mixture of trichloromethane and methanol (97:3 by volume) as eluent. The pure fractions were collected and the eluent was evaporated. From the residue the isomers were

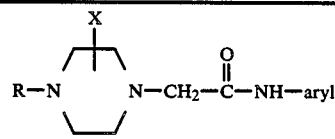

| Compound | R | X | aryl | Isomeric form | Salt or base form | mp. in °C. |
|---|---|---|---|---|---|---|
| 52 | (4-F—$C_6H_4$)$_2$CH—($CH_2$)$_3$— | 2-COO$C_2H_5$ | 2,6-($CH_3$)$_2$—$C_6H_3$— | — | (E)-2-butenedioate (1:1) | 173.6 |
| 53 | (4-F—$C_6H_4$)$_2$(COO$C_2H_5$)C—($CH_2$)$_3$— | 2-$CH_2$OH | 2,6-($CH_3$)$_2$—$C_6H_3$— | — | base | 53–87.5 |
| 54 | (4-F—$C_6H_4$)$_2$CH—($CH_2$)$_3$— | 3-$CH_2$OH | 2,6-($CH_3$)$_2$, 4-$NO_2$—$C_6H_2$— | — | base | — |
| 55 | (4-F—$C_6H_4$)$_2$CH—($CH_2$)$_3$— | 3-CONH$CH_3$ | 2,6-($CH_3$)$_2$, 4-$NO_2$—$C_6H_2$— | — | base | — |
| 56 | (4-F—$C_6H_4$)$_2$CH—($CH_2$)$_3$— | 3-CON$H_2$ | 2-COO$CH_3$—$C_6H_4$— | — | base | 186.0 |
| 57 | (4-F—$C_6H_4$)$_2$CH—($CH_2$)$_3$— | 3-CONH$CH_3$ | 2-$CH_3$, 4-$NO_2$—$C_6H_3$ | — | 2 HCl | 171.5 |
| 58 | (2-Cl—10H—phenothiazin-10-yl)-CO—$CH_2$—$CH_2$— | 3-CON$H_2$ | 2,6-$Cl_2$—$C_6H_3$— | — | base | 207.2 |
| 59 | (1,2,3,6-tetrahydro-1,3-($CH_3$)$_2$-2,6-dioxo-7H—purin-7-yl)-$CH_2$—$CH_2$— | 3-CON$H_2$ | 2,6-($CH_3$)$_2$—$C_6H_3$— | — | $H_2O$ | 147.6 |
| 60 | (4-F—$C_6H_4$)$_2$C=CH—($CH_2$)$_2$— | 3-CON$H_2$ | 2,6-$Cl_2$—$C_6H_3$— | — | 2HCl.$H_2O$ | 175.3 |
| 61 | (4-F—$C_6H_4$)$_2$C=CH—$CH_2$— | 3-CON$H_2$ | 2,6-($CH_3$)$_2$—$C_6H_3$— | — | base | 206.8 |
| 62 | $C_6H_5$—CH=CH—$CH_2$— | 3-CONH$CH_3$ | 2,6-($CH_3$)$_2$—$C_6H_3$— | — | 2 HCl | 219.0 |
| 63 | $C_6H_5$—CH=CH—$CH_2$— | 3-CON$H_2$ | 2,6-($CH_3$)$_2$—$C_6H_3$— | E | base | 201.5 |
| 64 | (4-F—$C_6H_4$)$_2$CH—($CH_2$)$_5$— | 3-CON$H_2$ | 2,6-$Cl_2$—$C_6H_3$— | — | 2 HCl.$H_2O$ | 215.9 |
| 65 | $C_6H_5$—CH=CH—$CH_2$— | 3-CON$H_2$ | 2-O$CH_3$—$C_6H_4$— | — | 2 HCl.$H_2O$ | 215.0 |
| 66 | (4-F—$C_6H_4$)(COO$C_2H_5$)C—($CH_2$)$_3$— | 3-CON$H_2$ | 2,6-$Cl_2$—$C_6H_3$— | — | 2 HCl.$H_2O$ | 206.1 |
| 67 | ($C_6H_5$)$_2$—N—($CH_2$)$_3$— | 3-CON$H_2$ | 2,6-$Cl_2$—$C_6H_3$— | — | ½ $CH_3$—CH—$CH_3$<br>\|<br>OH | 102.2 |
| 68 | ($C_6H_5$)$_2$N—CO—($CH_2$)$_2$— | 3-CON$H_2$ | 2,6-$Cl_2$—$C_6H_3$— | — | base | 163.9 |

Example XXXVIII

A mixture of 2.5 parts of [(2-naphthalenyloxy)methyl]oxirane, 3.31 parts of 3-(aminocarbonyl)-N-(2,6-dichlorophenyl)-1-piperazineacetamide, 45 parts of benzene and 20 parts of methanol was stirred first for 3 hours at room temperature and further for 30 hours at reflux. The reaction mixture was cooled and purified by column-chromatography over silica gel using a mixture of trichloromethane and methanol (90:10 by volume) as separated by HPLC using a mixture of methylbenzene and ethanol (95:5 by volume) as eluent. The fraction containing the B-isomer was collected and the eluent was evaporated. The residue was suspended in petroleumether. The product was filtered off and dried, yielding, after drying in vacuo at 145° C., 1.73 parts of (B)-3-(aminocarbonyl)-4-[4,4-bis(4-fluorophenyl)cyclohexyl]-N-(2,6-dimethylphenyl)-1-piperazineacetamide; mp. 212.1° C. (compound 71).

Example XL

A mixture of 4.05 parts of 2-chloro-N-(2,6-dichlorophenyl)acetamide, 5.6 parts of 1-[4,4-bis(4-fluorophenyl)butyl]-2-piperazinecarboxamide, 2.94 parts of N,N-diethylethanamine and 63 parts of N,N-dimethylformamide was stirred for 5 hours at 70° C. The reaction mixture was poured onto ice-water. The precipitated product was filtered off and dissolved in dichloromethane. The solution was washed with water, dried, filtered and evaporated. The residue was purified by column-chromatography over silica gel using a mixture of trichloromethane and methanol (95:5 by volume) as eluent. The pure fractions were collected and the eluent was evaporated. The residue was converted into the hydrochloride salt in 2-propanone and 2-propanol. The salt was filtered off and stirred for 30 minutes in 1,1'-oxybisethane, yielding 4.54 parts of 3-(aminocarbonyl)-4-[4,4-bis(4-fluorophenyl)butyl]-N-(2,6-dichlorophenyl)-1-piperazineacetamide dihydrochloride monohydrate; mp. 182.7° C. (compound 72).

Following the same N-alkylation procedure and using equivalent amounts of the appropriate starting materials there were also prepared:

$$R^1-C_nH_{2n}-N\underset{\diagup}{\overset{X}{\diagdown}}N-CH_2-\underset{}{\overset{O}{\underset{\|}{C}}}-\underset{R^2}{N}-aryl$$

| Com No. | R¹ | CₙH₂ₙ | X | R² | aryl | base or salt form | mp. °C. |
|---|---|---|---|---|---|---|---|
| 73 | C₆H₅— | CH₂ | 2-CONH₂— | H | 2,6-(CH₃)₂—C₆H₃— | base | 161.9 |
| 74 | (4-F—C₆H₄)₂CH— | (CH₂)₃ | 3-CONH₂— | H | 2,6-(CH₃)₂—C₆H₃— | 2(COOH)₂ | 217.3 |
| 75 | (C₆H₅)₂CH— | (CH₂)₃ | 2-COOC₂H₅— | H | 2,6-(CH₃)₂—C₆H₃— | base | — |
| 76 | (4-F—C₆H₄)₂CH— | (CH₂)₃ | 3-CONH₂— | H | 2-Cl—6-CH₃—C₆H₃— | 2 HCl | 220.5 |
| 77 | (4-F—C₆H₄)₂CH— | (CH₂)₃ | 3-CONH₂— | H | 2,6-(CH₃)₂—C₆H₃— | 2 HCl.H₂O | 198.7 |
| 78 | (4-F—C₆H₄)₂CH— | (CH₂)₃ | 3-CONH₂— | H | 2,6-(CH₃)₂—C₆H₃— | base | 78.3 |
| 79 | (4-F—C₆H₄)₂CH— | (CH₂)₃ | 3-CONH₂— | H | 2,5-(OCH₃)₂—C₆H₃— | 2 HCl | 208.2 |
| 80 | (4-F—C₆H₄)₂CH— | (CH₂)₃ | 3-CONH₂— | H | 2,6-Br₂—C₆H₃— | base | 83.5 |
| 81 | (4-F—C₆H₄)₂CH— | (CH₂)₃ | 3-CONH₂— | H | 2,5-(OCH₃)₂—C₆H₃— | base | 154.9 |
| 82 | (4-F—C₆H₄)₂CH— | (CH₂)₃ | 3-CONH₂— | H | 2,5-(CH₃)₂—C₆H₃— | 2 HCl.H₂O | 203.3 |
| 83 | (4-F—C₆H₄)₂CH— | (CH₂)₃ | 3-CONH₂— | H | 2-C₂H₅—C₆H₄— | 2 HCl.H₂O | 186.4 |
| 84 | (4-F—C₆H₄)₂CH— | (CH₂)₃ | 3-CONH₂— | CH₃ | 2,6-(CH₃)₂—C₆H₃— | 2 HCl.H₂O | 174.7 |
| 85 | (4-F—C₆H₄)₂CH— | (CH₂)₃ | 3-CONH₂— | H | 2-COCH₃—C₆H₄— | base | 121.7 |
| 86 | (4-F—C₆H₄)₂CH— | (CH₂)₃ | 2-CONHCH₃— | H | 2,6-(CH₃)₂—C₆H₃— | 2 HCl | 209.5 |
| 87 | (4-F—C₆H₄)₂CH— | (CH₂)₃ | 3-CONH₂— | H | 2-CF₃—C₆H₄— | base | 122.2 |
| 88 | (4-F—C₆H₄)₂CH— | (CH₂)₃ | 3-CONH₂— | H | 2-OCH₃—C₆H₄— | 2 HCl.½ H₂O | 211.1 |
| 89 | (4-F—C₆H₄)₂CH— | (CH₂)₃ | 3-CONH₂— | H | 2-OCH₃—5-CF₃—C₆H₃— | base | 162 |
| 90 | (4-F—C₆H₄)₂CH— | (CH₂)₃ | 3-CONH₂— | H | 2,6-F₂—C₆H₃— | 2 HCl.H₂O | 157-170 |
| 91 | (4-F—C₆H₄)₂CH— | (CH₂)₃ | 3-CONH₂— | H | 2-CH₃—5-F—C₆H₃— | 2 HCl.H₂O | 205.8 |
| 92 | (4-F—C₆H₄)₂CH— | (CH₂)₃ | 3-CONH₂— | H | 2-CH₃—5-Cl—C₆H₃— | 2 HCl.H₂O | 207-216 |
| 93 | (4-F—C₆H₄)₂CH— | (CH₂)₃ | 2-CONH₂— | H | 2,6-(C₂H₅)₂—C₆H₃— | base | 155.1 |
| 94 | (4-F—C₆H₄)₂CH— | (CH₂)₃ | 2-CONHCH₃— | H | 2,6-Cl₂—C₆H₃— | 2 HCl | 204.2 |
| 95 | (4-F—C₆H₄)₂CH— | (CH₂)₃ | 2-CONH₂— | H | 2-CH₃—4-OCH₃—C₆H₃— | base | 125.3 |
| 96 | (4-F—C₆H₄)₂CH— | (CH₂)₃ | 3-CONH₂— | H | 2-CH₃—4-OCH₃—C₆H₃— | base | 105.1 |
| 97 | (4-F—C₆H₄)₂CH— | (CH₂)₃ | 2-CH₂OH— | H | 2,6-(CH₃)₂—4-NO₂—C₆H₂— | base | 121.0 |
| 98 | (4-F—C₆H₄)₂CH— | (CH₂)₃ | 3-CONH₂— | H | 2-Cl—C₆H₄— | base | 154.0 |
| 99 | (4-F—C₆H₄)₂CH— | (CH₂)₃ | 2-CONHCH₂CH₂OH— | H | 2,6-Cl₂—C₆H₃— | ½ H₂O | 143.2 |
| 100 | (4-F—C₆H₄)₂CH— | (CH₂)₃ | 2-CH₂OH— | H | 2-Cl—6-CH₃—C₆H₃— | base | 56.1 |
| 101 | (4-F—C₆H₄)₂CH— | (CH₂)₃ | 3-CONH₂— | H | 2,6-Cl₂—4-CN—C₆H₂— | 2 HCl.H₂O | 205-212 |
| 102 | (4-F—C₆H₄)₂CH— | (CH₂)₃ | 3-CONH₂— | H | 2,6-Cl₂—4-NO₂—C₆H₂— | 2 HCl.H₂O | 202-212.5 |
| 103 | (4-F—C₆H₄)₂CH— | (CH₂)₃ | 3-CONH₂— | H | 2,6-Cl₂—4-COCH₃—C₆H₂— | 2 HCl.H₂O | 168-182 |
| 104 | (4-F—C₆H₄)₂CH— | (CH₂)₃ | 3-CONH₂— | H | 2,4-(OCH₃)₂—5-Cl—C₆H₂— | 2 HCl | 203.5-209 |
| 105 | (4-F—C₆H₄)₂CH— | (CH₂)₃ | 3-CONH₂— | H | 2,6-Cl₂—4-CONH₂—C₆H₂— | 2 HCl | 237.1 |
| 106 | (4-F—C₆H₄)₂CH— | (CH₂)₃ | 3-CONH₂— | H | 2,6-(C₂H₅)₂—C₆H₃— | 2 HCl | 220-225 |
| 107 | (4-F—C₆H₄)₂CH— | (CH₂)₃ | 3-CONH₂— | H | 2,6-(CH₃)₂—4-OH—C₆H₂— | 2 HCl.H₂O | 175-202 |

In a similar manner there were also prepared:

$$R-N\underset{\diagup}{\overset{X}{\diagdown}}N-CH_2-\overset{O}{\underset{\|}{C}}-NH-aryl$$

| Compound No. | R | X | aryl | Isomeric form | Salt or base form | mp. in °C. |
|---|---|---|---|---|---|---|
| 108 | (4-F—C₆H₄)₂CH(CH₂)₃— | 3-CONH₂ | 5-Cl, 2-OCH₃, 4-NO₂C₆H₂— | — | 2 HCl.H₂O | — |
| 109 | (4-F—C₆H₄)₂CH(CH₂)₃— | 3-CONH₂ | 4-F—C₆H₄— | — | 2 HCl | 212.8 |
| 110 | C₆H₅—CH=CH—CH₂— | 2-CONH₂ | 2,6-(CH₃)₂—C₆H₃— | E | 2 HCl.½ H₂O | 192.0 |
| 111 | C₆H₅—CH=CH—CH₂— | 2-CONH₂ | 5-F,2-CH₃—C₆H₃— | — | ½ H₂O | 125.3 |
| 112 | (4-F—C₆H₄)₂CH(CH₂)₃— | 2-COOC₂H₅ | 2,6-Cl₂—C₆H₃— | — | base | 123.7 |

Example XLI

A mixture of 24.0 parts of α-methyl-4-(phenylmethyl)-2-piperazinemethanol, 27.3 parts of 2-chloro-N-(2,6-dimethylphenyl)acetamide, 25.4 parts of sodium carbonate, 0.1 parts of potassium iodide and 180 parts of N,N-dimethylformamide was stirred for 18 hours at 60° C. The reaction mixture was poured onto water and the product was extracted with dichloromethane. The extract was washed with water, dried, filtered and evaporated. The residue was purified by column-chromatography over silica gel using a mixture of trichloromethane and methanol (90:10 by volume) as eluent. The pure fractions were collected and the eluent was evaporated. The residue was crystallized from 1,1'-oxybisethane, yielding 35.19 parts (84.8%) of N-(2,6-dimethylphenyl)-2-(1-hydroxyethyl)-4-(phenylmethyl)-1-piperazineacetamide; mp. 148.8° C. (compound 113).

Following the same N-alkylation procedure and using equivalent amounts of the appropriate starting materials there were also prepared:

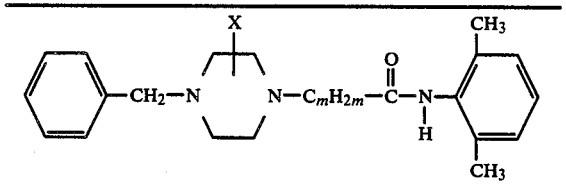

| Compound | X | $C_mH_{2m}$ | Stereochemically isomeric form | Base or Salt form | mp. °C. |
|---|---|---|---|---|---|
| 114 | 2-CH$_2$OH | CH$_2$ | | base | — |
| 115 | 2-CH$_2$OCH$_3$ | CH$_2$ | | base | — |
| 116 | 2-CON(CH$_3$)$_2$ | CH$_2$ | | 2 HCl | 240 |
| 117 | 2-CH$_2$OC$_2$H$_5$ | CH(CH$_3$) | A + B | base | — |
| 118 | 2-CH$_2$OC$_2$H$_5$ | CH$_2$ | | base | — |

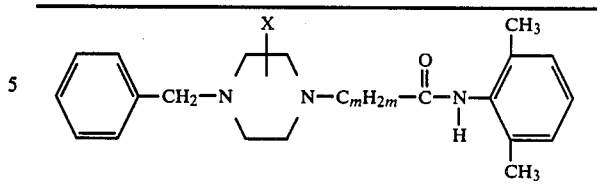

| Compound | X | $C_mH_{2m}$ | Stereochemically isomeric form | Base or Salt form | mp. °C. |
|---|---|---|---|---|---|
| 119 | 2-CH$_2$CONH$_2$ | CH$_2$ | | base | — |
| 120 | 2-CH(CH$_3$)OCH$_3$ | CH$_2$ | B | base | — |
| 121 | 2-CH(CH$_3$)OCH$_3$ | CH$_2$ | A | base | — |

Example XLII

A mixture of 3.7 parts of 1-[4,4-bis(4-fluorophenyl)butyl]-2-piperazinecarboxamide, 2.3 parts of 3-chloro-N-(2,6-dimethylphenyl)propanamide, 2.1 parts of sodium carbonate, 0.1 parts of potassium iodide and 200 parts of 4-methyl-2-pentanone was stirred and refluxed for 20 hours using a water-separator. The reaction mixture was cooled to room temperature and filtered. The filtrate was evaporated. The oily residue was purified by column-chromatography over silica gel using a mixture of trichloromethane and methanol (95:5 by volume) as eluent. The pure fractions were collected and the eluent was evaporated. The residue solidified on triturating in 2,2'-oxybispropane. The product was filtered off and dried, yielding 3.87 parts (70.8%) of 3-(aminocarbonyl)-4-[4,4-bis(4-fluorophenyl)butyl]-N-(2,6-dimethylphenyl)-1-piperazinepropanamide; mp. 120.9° C. (compound 122)

Following the same N-alkylation procedure and using equivalent amounts of the appropriate starting materials there were also prepared:

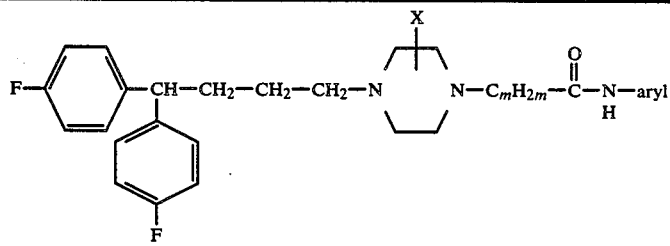

| Compound | X | $C_mH_{2m}$ | aryl | Base or Salt form | mp. in °C. |
|---|---|---|---|---|---|
| 123 | 3-CH$_2$OH | CH$_2$ | 2,6-(CH$_3$)$_2$—C$_6$H$_3$— | base | 150.2 |
| 124 | 3-CON(CH$_3$)$_2$ | CH$_2$ | 2,6-(CH$_3$)$_2$—C$_6$H$_3$— | 2 HCl.2 H$_2$O | 195.3 |
| 125 | 3-CH$_2$OCH$_3$ | CH$_2$ | 2,6-(CH$_3$)$_2$—C$_6$H$_3$— | 2 HCl.H$_2$O | 178.1 |
| 126 | 3-CONH$_2$ | CH$_2$ | 2-CH$_3$—4-NH$_2$—C$_6$H$_3$— | base | 84.4 |
| 127 | 3-CONH$_2$ | CH$_2$ | 2,4-Cl$_2$—C$_6$H$_3$— | base | 274.9 |
| 128 | 3-CONH$_2$ | CH$_2$ | 2-CH$_3$—4-NO$_2$—C$_6$H$_3$— | 2 HCl.H$_2$O | 203.2 |
| 129 | 3-CONH$_2$ | CH$_2$—CH$_2$ | 2,6-Cl$_2$—C$_6$H$_3$— | base | 79.4 |
| 130 | 3-CONH$_2$ | CH(CH$_3$) | 2,6-Cl$_2$—C$_6$H$_3$— | base | 91.9 |
| 131 | 3-CONH$_2$ | CH(CH$_3$) | 2,6-(CH$_3$)$_2$—C$_6$H$_3$— | base | 84.3 |
| 132 | 2-CONH$_2$ | CH$_2$ | 2,6-Cl$_2$—C$_6$H$_3$— | base | 182.2 |
| 133 | 2-CONH$_2$ | CH$_2$ | 2-Cl—C$_6$H$_4$— | base | 151.3 |
| 134 | 2-CONH$_2$ | CH$_2$ | 2,5-Cl$_2$—C$_6$H$_3$— | base | 112.3 |
| 135 | 2-COHN$_2$ | CH$_2$ | 2-CH$_3$, 5-Cl—C$_6$H$_3$— | base | 143.8 |
| 136 | 3-CONH$_2$ | CH$_2$ | 2,5-Cl$_2$—C$_6$H$_3$— | 2 HCl | 198.0-202.5 |
| 137 | 2-CONH$_2$ | CH$_2$—CH$_2$ | 2,6-(CH$_3$)$_2$—C$_6$H$_3$— | base | 103.7 |
| 138 | 2-CONH$_2$ | CH(CH$_3$) | 2,6-(CH$_3$)$_2$—C$_6$H$_3$— | base | 92.8 |
| 139 | 2-CONH$_2$ | CH$_2$ | 2-Cl—6-CH$_3$—C$_6$H$_3$— | base | 197.6 |
| 140 | 2-CONH$_2$ | CH$_2$ | 2-CH$_3$—5-F—C$_6$H$_3$— | base | 102.2 |
| 141 | 2-CONH$_2$ | CH$_2$—CH$_2$ | 2,6-Cl$_2$—C$_6$H$_3$— | base | 83.7 |

-continued

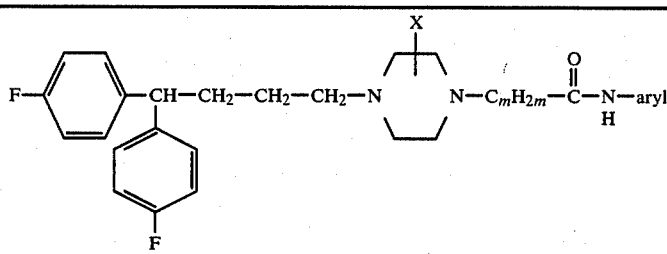

| Compound | X | $C_mH_{2m}$ | aryl | Base or Salt form | mp. in °C. |
|---|---|---|---|---|---|
| 142 | 2-CONHCH$_2$CH$_2$OH | CH$_2$ | 2,6-(CH$_3$)$_2$—C$_6$H$_3$— | 2 HCl | 188–193 (dec.) |
| 143 | 2-CONHCH(CH$_3$)$_2$ | CH$_2$ | 2,6-(CH$_3$)$_2$—C$_6$H$_3$— | base | 156.4 |
| 144 | 2-CONHCH(CH$_3$)$_2$ | CH$_2$ | 2,6-Cl$_2$—C$_6$H$_3$— | base | 171.2 |
| 145 | 2-CONHCH$_3$ | CH$_2$ | 2,6-(CH$_3$)$_2$—4-NO$_2$—C$_6$H$_2$— | base | 107 |
| 146 | 3-CONH$_2$ | CH$_2$ | 2,6-Cl$_2$—C$_6$H$_3$— | 2 HCl | — |
| 147 | 2-CONH—CH$_3$ | CH$_2$ | 2-CH$_3$—6-Cl—C$_6$H$_3$— | base | 137.6 |
| 148 | 2-CH$_2$OCH$_3$ | CH$_2$ | 2,6-Cl$_2$—C$_6$H$_3$— | 2 HCl | 134.4 |
| 149 | 2-CONH—CH$_3$ | CH$_2$ | 2-CH$_3$—4-NH$_2$—C$_6$H$_3$— | base | 89.2–96.8 |
| 150 | 2-CONH—CH$_3$ | CH$_2$ | 2,4,6-(CH$_3$)$_3$—C$_6$H$_2$— | base | 90.2 |
| 151 | 2-CONH—CH$_3$ | CH$_2$ | 2-CH$_3$—5-Cl—C$_6$H$_3$— | base | 146.3 |
| 152 | 3-CONH$_2$ | CH$_2$ | C$_6$H$_5$— | 2 HCl | 205.0–211.5 |
| 153 | 3-CONH$_2$ | CH$_2$ | 4-NO$_2$—C$_6$H$_4$— | 2 HCl.H$_2$O | 200.0 |

Example XLIII

During 5 hours, gaseous hydrogen chloride was bubbled through a stirred and refluxing mixture of 5 parts of 1-[4,4-bis(4-fluorophenyl)butyl]-4-[2-[(2,6-dimethylphenyl)amino]-2-oxoethyl]-2-piperazinecarboxylic acid and 200 parts of absolute ethanol. After standing overnight at room temperature, the reaction mixture was evaporated. The residue was taken up in 200 parts of water and alkalized with sodium hydroxide. The product was extracted twice with 80 parts of 4-methyl-2-pentanone. The combined extracts were dried, filtered and evaporated. The residue was purified twice by column-chromatography over silica gel using a mixture of trichloromethane and methanol (90:10 by volume) as eluent. The pure fractions were collected and the eluent was evaporated. The residue was converted into the hydrochloride salt in ethanol and 2-propanol. The solvent was evaporated and the semi-solid residue was dissolved in a mixture of 16 parts of 2-propanone and 2 parts of water. The whole was evaporated. The solid residue was pulverized and dried, yielding 2.37 parts (40%) of ethyl 1-[4,4-bis(4-fluorophenyl)butyl[4-[2-[(2,6-dimethylphenyl)amino]-2-oxoethyl]-2-piperazinecarboxylate dihydrochloride hemihydrate; mp. 118.8° C. (compound 154).

Example XLIV

A mixture of 52 parts of ethyl 1-[4,4-bis(4-fluorophenyl)butyl]-4-[2-[(2,6-dimethylphenyl)amino]-2-oxoethyl]-2-piperazinecarboxylate and 600 parts of concentrated hydrochloric acid was stirred for 8 hours in a boiling water-bath. The reaction mixture was concentrated to a volume of about 200 parts. The supernatant aqueous phase was decanted and the oily residue was dissolved in 400 parts of 2-propanone and 500 parts of water. The whole was neutralized by the portionwise addition of sodium hydrogen carbonate. The 2-propanone was evaporated on a Rotavapor. The aqueous phase was decanted and the residue was triturated in warm 4-methyl-2-pentanone. After cooling, the product was filtered off and dissolved in 200 parts of methanol while heating. After cooling, 250 parts of water were added and the whole was stirred for a while. The solid product was filtered off and crystallized from acetonitrile, yielding, after drying in vacuo for 3 hours at 110° C., 16.32 parts of 1-[4,4-bis(4-fluorophenyl)butyl]-4-[2-[(2,6-dimethylphenyl)amino]-2-oxoethyl]-2-piperazinecarboxylic acid; mp. 186.5° C. (compound 155).

Example XLV

To 1 part of a solution of 2 parts of thiophene in 40 parts of ethanol were added 3.4 parts of 4-[4,4-bis(4-fluorophenyl)butyl]-N-(2,6-dimethyl-4-nitrophenyl)-2-(hydroxymethyl)-1-piperazineacetamide and 120 parts of methanol. The whole is hydrogenated at normal pressure and at room temperature with 2 parts of platinum-on-charcoal catalyst 5%. After the calculated amount of hydrogen was taken up, the catalyst was filtered off and the filtrate was evaporated. The oily residue was purified by column-chromatography over silica gel using a mixture of trichloromethane and methanol (90:10 by volume) as eluent. The pure fractions were collected and the eluent was evaporated. The oily residue solidified on cooling in a 2-propanone/CO$_2$-bath. The product was dried, yielding 1.73 parts (54%) of N-(4-amino-2,6-dimethylphenyl)-4-[4,4-bis(4-fluorophenyl)butyl]-2-(hydroxymethyl)-1-piperazineacetamide; mp. 85.2° C. (compound 156).

In a similar manner there were also prepared:

3-(aminocarbonyl)-N-(4-amino-2,6-dimethylphenyl)-4-[4,4-bis(4-fluorophenyl)butyl]-1-piperazineacetamide; mp. 114.4° C. (compound 157);

N-(4-amino-2,6-dimethylphenyl)-4-[4,4-bis(4-fluorophenyl)butyl]-3-(hydroxymethyl)-1-piperazineacetamide; mp. 81.3° C. (compound 158);

N-(4-amino-2-methylphenyl)-4-[4,4-bis(4-fluorophenyl)butyl]-3-[(methylamino)carbonyl]-1-piperazineacetamide; mp. 86.2° C. (compound 159);

3-(aminocarbonyl)-N-(4-amino-2,6-dichlorophenyl)-4-[4,4-bis(4-fluorophenyl)butyl]-1-piperazineacetamide dihydrochloride dihydrate; mp. 196.3° C. (compound 160); and 3-(aminocarbonyl)-N-(4-amino-5-chloro-2-methoxyphenyl)-4-[4,4-bis(4-fluorophenyl)butyl]-1-piperazineacetamide; mp. 189.3° C. (compound 161).

Example XLVI

To 1 part of a solution of 2 parts of thiophene in 40 parts of ethanol were added 3 parts of 4-[4,4-bis(4-fluorophenyl)butyl]-N-(2,6-dimethyl-4-nitrophenyl)-2-[(methylamino)carbonyl]-1-piperazineacetamide and 120 parts of methanol. The whole was hydrogenated at normal pressure and at room temperature with 2 parts of palladium-on-charcoal catalyst 10%. After the calculated amount of hydrogen was taken up, the catalyst was filtered off and the filtrate was evaporated. The residue was purified by column-chromatography over silica gel using a mixture of trichloromethane and methanol (95:5 by volume) as eluent. The pure fractions were collected and the eluent was evaporated. The residue was suspended in 2,2'-oxybispropane, yielding 2.14 parts of N-(4-amino-2,6-dimethylphenyl)-4-[4,4-bis(4-fluorophenyl)butyl]-2-[(methylamino)carbonyl]-1-piperazineacetamide; mp. 111.7° C. (compound 162).

In a similar manner there were also prepared:
N-(4-amino-2,6-dimethylphenyl)-4-[4,4-bis(4-fluorophenyl)butyl]-3-[(methylamino)carbonyl]-1-piperazineacetamide; mp. 88.7° C. (compound 163); and
3-(aminocarbonyl)-N-(4-aminophenyl)-4-[4,4-bis(4-fluorophenyl)butyl]-1-piperazineacetamide monohydrate; mp. 90.1° C. (compound 164).

Example XLVII

A mixture of 5.5 parts of 3-(aminocarbonyl)-N-(4-amino-2,6-dimethylphenyl)-4-[4,4-bis(4-fluorophenyl)butyl]-1-piperazineacetamide, 8 parts of 2-propanone, 1 part of a solution of thiophene in ethanol 4% and 120 parts of methanol was hydrogenated at normal pressure and at room temperature with 2 parts of palladium-on-charcoal catalyst 10%. After the calculated amount of hydrogen was taken up, the catalyst was filtered off and the filtrate was evaporated. The residue was suspended in 2,2'-oxybispropane. The product was filtered off and dried, yielding 4.5 parts of 3-(aminocarbonyl)-4-[4,4-bis(4-fluorophenyl)butyl]-N-[[2,6-dimethyl-4-[(1-methylethyl)amino]phenyl]-1-piperazineacetamide monohydrate; mp. 100.7° C. (compound 165).

Example XLVIII

A mixture of 5.5 parts of 3-(aminocarbonyl)-N-(4-amino-2,6-dimethylphenyl)-4-[4,4-bis(4-fluorophenyl)butyl]-1-piperazineacetamide, 1 part of a solution of thiophene in ethanol 5%, 3 parts of poly(oxymethylene) and 120 parts of methanol was hydrogenated at normal pressure and at room temperature with 2 parts of palladium-on-charcoal catalyst 10%. After the calculated amount of hydrogen was taken up, the catalyst was filtered off and the filtrate was evaporated. The residue was taken up in a diluted hydrochloric acid solution and the whole was washed with 2,2'-oxybispropane. The aqueous phase was alkalized and extracted with dichloromethane. The combined organic phases were washed with water, dried, filtered and evaporated. The residue was converted into the hydrochloride salt in acetonitrile and 2-propanol. The salt was filtered off and crystallized from 2-propanol, yielding 2.86 parts of 3-(aminocarbonyl)-4-[4,4-bis(4-fluorophenyl)butyl]-N-[4-(dimethylamino)-2,6-dimethylphenyl]-1-piperazineacetamide trihydrochloride monohydrate; mp. 194.5° C. (compound 166).

In a similar manner there was also prepared:
3-(aminocarbonyl)-4-[4,4-bis(4-fluorophenyl)butyl]-N-[4-(dimethylamino)phenyl]-1-piperazineacetamide monohydrate; mp. 96.3° C. (compound 167).

Example IL

To a stirred solution of 5.5 parts of 3-(aminocarbonyl)-N-(4-amino-2,6-dimethylphenyl)-4-[4,4-bis(4-fluorophenyl)butyl]-1-piperazineacetamide in 70 parts of acetic acid was added dropwise a solution of 1.62 parts of potassium isocyanate in 20 parts of water. Upon completion, stirring at room temperature was continued for 30 minutes. Upon standing overnight at room temperature, the reaction mixture was evaporated. Water was added to the residue and the product was extracted with dichloromethane. The extract was washed with water, dried, filtered and evaporated. The residue was purified by column-chromatography over silica gel using a mixture of trichloromethane and methanol (90:10 by volume) as eluent. The pure fractions were collected and the eluent was evaporated. The residue was crystallized from acetonitrile, yielding 2.55 parts of 3-(aminocarbonyl)-N-[4-[(aminocarbonyl)amino]-2,6-dimethylphenyl]-4-[4,4-bis(4-fluorophenyl)butyl]-1-piperazineacetamide; mp. 142.5° C. (compound 168).

Example L

A mixture of 5.5 parts of 3-(aminocarbonyl)-N-(4-amino-2,6-dimethylphenyl)-4-[4,4-bis(4-fluorophenyl)butyl]-1-piperazineacetamide, 1.82 parts of propanoic acid anhydride and 90 parts of methylbenzene was stirred and refluxed for 20 hours. Water was added to the reaction mixture and the layers were separated. The organic phase was washed with a sodium carbonate solution and with water, dried, filtered and evaporated. The residue was purified by column-chromatography over silica gel using a mixture of trichloromethane and methanol (95:5 by volume) as eluent. The first fraction was collected and the eluent was evaporated. The residue was suspended in 2,2'-oxybispropane. The product was filtered off and crystallized from acetonitrile, yielding 1.38 parts of N-[4-[[2-[3-aminocarbonyl)-4-[4,4-bis(4-fluorophenyl)butyl]-1-piperazinyl]acetyl]amino]-3,5-dimethylphenyl]propanamide monohydrate; mp. 136° C. (compound 169).

Example LI

A mixture of 4 parts of 3-(aminocarbonyl)-4-[3,3-bis(4-fluorophenyl)-2-propenyl]-N-(2,6-dimethylphenyl)-1-piperazineacetamide and 120 parts of methanol was hydrogenated at normal pressure and at room temperature with 2 parts of palladium-on-charcoal catalyst 10%. After the calculated amount of hydrogen was taken up, the catalyst was filtered off and the filtrate was evaporated. The residue was purified by column-chromatography over silica gel using a mixture of trichloromethane and methanol (90:10 by volume) as eluent. The pure fractions were collected and the eluent was evaporated. The residue was suspended in 2,2'-oxybispropane. The product was filtered off and dissolved in acetonitrile. The solution was filtered and the filtrate was evaporated. The residue was crystallized from 2,2'-oxybispropane. The product was filtered off and dried, yielding 2.21 parts of 3-(aminocarbonyl)-4-[3,3-bis(4-fluorophenyl)propyl]-N-(2,6-dimethylphenyl)-1-piperazineacetamide; mp. 143.2° C. (compound 170).

Example LII

A mixture of 4.45 parts of 5-chloro-1,1-diphenyl-2-pentanone, 9.94 parts of 3-(aminocarbonyl)-N-(2,6-dichlorophenyl)-1-piperazineacetamide and 90 parts of N,N-dimethylformamide was stirred for 48 hours at 60° C. and evaporated. The residue was taken up in water and alkalized with ammonia. The product was extracted twice with dichloromethane. The combined extracts were washed with water, dried, filtered and evaporated. The residue was purified twice by column-chromatography over silica gel using a mixture of trichloromethane and methanol (95:5 by volume) as eluent. The pure fractions were collected and the eluent was evaporated. The residue was taken up in 2,2'-oxybispropane and allowed to stand for 10 days. The product was filtered off and dried at the air, yielding 0.32 parts (3.7%) of 3-(aminocarbonyl)-N-(2,6-dichlorophenyl)-4-(4-oxo-5,5-diphenylpentyl)-1-piperazineacetamide monohydrate; mp. 91.6° C. (compound 171).

Example LIII

A mixture of 3.3 parts of ethyl 1-[4,4-bis(4-fluorophenyl)butyl]-4-[2-[(2,6-dichlorophenyl)amino]-2-oxoethyl]-2-piperazinecarboxylate and 60 parts of a hydrochloric acid solution 12N was stirred for 8 hours at 100° C. in an oil-bath. 2-Propanone was added whereupon a solution was obtained. The pH was adjusted to 5 with sodium hydrogen carbonate and the 2-propanone was evaporated: a sticky oil in water was remained. The aqueous phase was decanted and the sticky oil was taken up in 24 parts of 4-methyl-2-pentanone while warming. The solid product was filtered off and boiled in 120 parts of acetonitrile. After cooling for a while, the less pure product was filtered off and the filtrate was cooled. The product was filtered off and dried, yielding 0.31 parts of 1-[4,4-bis(4-fluorophenyl)butyl]-4-[2-[(2,6-dichlorophenyl)amino]-2-oxoethyl]-2-piperazinecarboxylic acid; mp. 204.3° C. (compound 172).

Example LIV

To a stirred solution of 3 parts of 3-(aminocarbonyl)-4-[4,4-bis(4-fluorophenyl)butyl]-N-(2,6-dimethylphenyl)-1-piperazineacetamide in 24 parts of ethanol was added a solution of 0.94 parts of (+)-2,3-dihydroxybutanedioic acid in 24 parts of ethanol. The whole was evaporated and the oily residue was dissolved in warm 4-methyl-2-pentanone. After cooling to 0° C., the product was filtered off and dissolved in 2-propanone. 0.2 Parts of 2,3-dihydroxybutanedioic acid were added and upon the addition of 4-methyl-2-pentanone, the product was precipitated. It was filtered off and dried, yielding 0.8 parts of (+)-3-(aminocarbonyl)-4-[4,4-bis(4-fluorophenyl)butyl]-N-(2,6-dimethylphenyl)-1-piperazineacetamide [R-(R*,R*)]-2,3-dihydroxybutanedioate (2:3) monohydrate; mp. 78.1° C. (compound 173).

Example LV

A solution of 3 parts of 3-(aminocarbonyl)-4-[4,4-bis(4-fluorophenyl)butyl]-N-(2,6-dimethylphenyl)-1-piperazineacetamide in 80 parts of 2-propanone was added to a solution of 1.9 parts of (Z)-2-butenedioate in 40 parts of 2-propanone: slowly crystallization. The product was filtered off and recrystallized twice from 2-propanol and once from 2-propanone, yielding 1.56 parts (39%) of 3-(aminocarbonyl)-4-[4,4-bis(4-fluorophenyl)butyl]-N-(2,6-dimethylphenyl)-1-piperazineacetamide (Z)-2-butenedioate (1:2) monohydrate; mp. 119.6° C. (compound 174).

What is claimed is:

1. A chemical compound having the formula

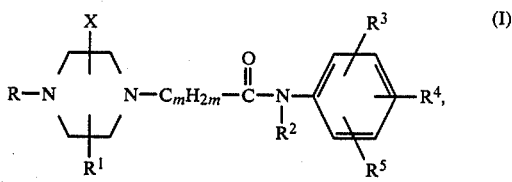

the stereochemically isomeric forms and the pharmaceutically acceptable acid addition salts thereof, wherein $R^1$ is a member selected from the group consisting of hydrogen and lower alkyl;

X is a member selected from the group consisting of hydroxylower alkyl, lower alkyloxylower alkyl, aminocarbonyl, mono- and di(lower alkyl)aminocarbonyl, carboxyl, lower alkyloxycarbonyl, (aminocarbonyl)lower alkyl, [mono- and di(lower alkyl)aminocarbonyl]lower alkyl, carboxylower alkyl, (lower alkyloxycarbonyl)lower alkyl and (hydroxylower alkyl)aminocarbonyl;

m is the integer 1 or 2;

$R^2$ is a member selected from the group consisting of hydrogen and lower alkyl;

$R^3$, $R^4$ and $R^5$ are each independently selected from the group consisting of hydrogen, hydroxy, lower alkyl, lower alkyloxy, halo, trifluoromethyl, lower alkylcarbonyl, aminocarbonyl, lower alkyloxycarbonyl, mono- and di(lower alkyl)amino, amino and (aminocarbonyl)amino, while $R^3$ may also be nitro cyano or amino; and R is a member selected from the group consisting of a radical having the formula —Alk—Q         (b)

wherein

Alk is an alkanediyl radical or a lower alkenediyl radical, said lower alkanediyl radical being optionally substituted by a hydroxy- or a lower alkyl radical; and Q is a member selected from the group consisting of aryl, aryloxy, diarylmethoxy, 2,2-diarylethenyl, diarylmethylcarbonyl, mono- and diarylaminocarbonyl, diarylmethyl, the methyl moiety in said diarylmethyl group being optionally substituted with a cyano-, or a lower alkyloxycarbonyl radical, arylamino, said amino moiety being optionally substituted with an aryl, radical, 2,3-dihydro-2-oxo-1H-benzimidazol-1-yl, being optionally substituted in the 5- or 6-position by halo, and 1-aryl-1,3-dihydroisobenzofuran-1-yl, wherein aryl is a member selected from the group consisting of phenyl, substituted phenyl, naphthalenyl, thienyl and pyridinyl, said substituted phenyl having from 1 to 2 substituents, each independently selected from the group consisting of halo and (halo-substituted phenyl)carbonyl.

2. A chemical compound having the formula

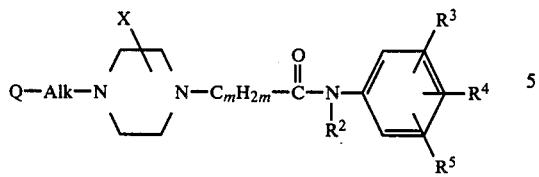

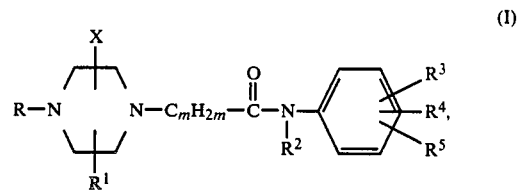

the stereochemically isomeric forms and the pharmaceutically acceptable acid addition salts thereof, wherein $R^2$ is a member selected from the group consisting of hydrogen and lower alkyl;

X is a member selected from the group consisting of hydroxyloweralkyl, aminocarbonyl, and (lower alkyl)aminocarbonyl;

m is the integer 1 or 2;

$R^3$, $R^4$ and $R^5$ are each independently selected from the group consisting of hydrogen, hydroxy, lower alkyl, lower alkyloxy, halo, trifluoromethyl, lower alkylcarbonyl, aminocarbonyl, lower alkyloxycarbonyl, mono- and di(lower alkyl)amino, and (aminocarbonyl)amino, while $R^3$ and/or $R^4$ may also be nitro, cyano or amino and Alk is an alkanediyl radical or a lower alkanediyl radical, said lower alkanediyl radical being optionally substituted by a hydroxy- or a lower alkyl radical; and Q is a member selected from the group consisting of aryl; diarylmethyl, the methyl moiety in said diarylmethyl group being optionally substituted with a cyano or a lower alkyloxycarbonyl radical; diarylamino; and 1-aryl-1,3-dihydroisobenzofuran-1-yl, wherein aryl is a member selected from the group consisting of phenyl, substituted phenyl, and pyridinyl, said substituted phenyl having from 1 to 2 independently selected halo substituents.

3. A chemical compound according to claim 2 wherein Q is diarylmethyl and Alk is a 1,3-propanediyl radical.

4. A chemical compound according to claim 2 wherein Q is diarylmethyl and Alk is 1,3-$R^2$ is propanediyl, X is aminocarbonyl, m is 1 and hydrogen.

5. A chemical compound according to claim 2 wherein Q is diarylmethyl, aryl is phenyl or substituted phenyl, X is aminocarbonyl, and $R^2$ is hydrogen.

6. A chemical compound selected from the group consisting of 3-(aminocarbonyl)-4-[4,4-bis(4-fluorophenyl)butyl]-N-(2,6-dichlorophenyl)-1-piperazineacetamide, the stereochemically isomeric forms and the pharmaceutically acceptable acid addition salts thereof.

7. A pharmaceutical composition in dosage unit form comprising per dosage unit an amount, effective in ameliorating the blood perfusion of the muscular tissues of the heart and/or effective in protecting, partially or completely, the heart from myocardial injury caused by more or less brief episodes of ischaemia, anoxia or hypoxia, of a compound having the formula the stereochemically isomeric forms and the pharmaceutically acceptable acid addition salts thereof, wherein $R^1$ is a member selected from the group consisting of hydrogen and lower alkyl;

X is a member selected from the group consisting of hydroxylower alkyl, lower alkyloxylower alkyl, aminocarbonyl, mono- and di(lower alkyl)aminocarbonyl, carboxyl, lower alkyloxycarbonyl, (aminocarbonyl)lower alkyl, [mono- and di(lower alkyl)aminocarbonyl]lower alkyl, carboxylower alkyl, (lower alkyloxycarbonyl)lower alkyl and (hydroxylower alkyl)aminocarbonyl;

m is the integer 1 or 2;

$R^2$ is a member selected from the group consisting of hydrogen and lower alkyl;

$R^3$, $R^4$ and $R^5$ are each independently selected from the group consisting of hydrogen, hydroxy, lower alkyl, lower alkyloxy, halo, trifluoromethyl, lower alkylcarbonyl, aminocarbonyl, lower alkyloxycarbonyl, mono- and di(lower alkyl)amino, amino and (aminocarbonyl)amino, while $R^3$ may also be nitro cyano or amino; and R is a member selected from the group consisting of a radical having the formula —Alk—Q (b)

wherein

Alk is an alkanediyl radical or a lower alkenediyl radical, said lower alkanediyl radical being optionally substituted by a hydroxy- or a lower alkyl radical; and Q is a member selected from the group consisting of aryl, aryloxy, diarylmethoxy, 2,2-diarylethenyl, diarylmethylcarbonyl, mono- and diarylaminocarbonyl, diarylmethyl, the methyl moiety in said diarylmethyl group being optionally substituted with a cyano-, or a lower alkyloxycarbonyl radical, arylamino, said amino moiety being optionally substituted with an aryl, radical, 2,3-dihydro-2-oxo-1H-benzimidazol-1-yl, being optionally substituted in the 5- or 6-position by halo, and 1-aryl-1,3-dihydroisobenzofuran-1-yl;

wherein aryl is a member selected from the group consisting of phenyl, substituted phenyl, naphthalenyl, thienyl and pyridinyl, said substituted phenyl having from 1 to 2 substituents, each independently selected from the group consisting of halo and (halo-substituted phenyl)carbonyl.

8. A pharmaceutical composition in dosage unit form comprising per dosage unit an amount effective in ameliorating the blood perfusion of the muscular tissues of the heart and/or effective in protecting, partially or completely, the heart from myocardial injury caused by more or less brief episodes of ischaemia, anoxia or hypoxia, of a compound having the formula

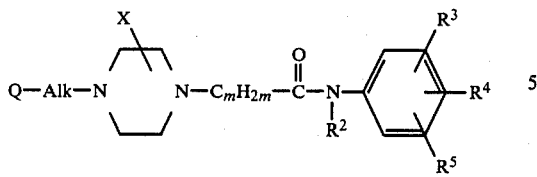

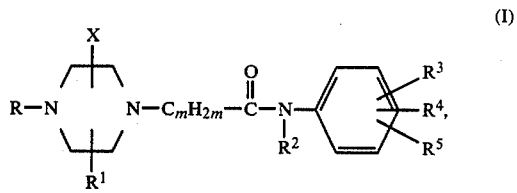

the stereochemically isomeric forms and the the pharmaceutically acceptable acid addition salts thereof, wherein $R_2$ is a member selected from the group consisting of hydrogen and lower alkyl;

X is a member selected from the group consisting of hydroxyloweralkyl, aminocarbonyl, and (lower alkyl)aminocarbonyl;

m is the integer 1 or 2;

$R^3$, $R^4$ and $R^5$ are each independently selected from the group consisting of hydrogen, hydroxy, lower alkyl, lower alkyloxy, halo, trifluoromethyl, lower alkylcarbonyl, aminocarbonyl, lower alkyloxycarbonyl, mono- and di(lower alkyl)amino, and (aminocarbonyl)amino, while $R^3$ and/or $R^4$ may also be nitro, cyano or amino; and Alk is an alkanediyl radical or a lower alkanediyl radical, said lower alkanediyl radical being optionally substituted by a hydroxy- or a lower alkyl radical; and Q is a member selected form the group consisting of aryl; diarylmethyl, the methyl moiety in said diarylmethyl group being optionally substituted with a cyano or a lower alkyloxycarbonyl radical; diarylamino; and 1-aryl-1,3-dihydroisobenzofuran-1-yl;

wherein aryl is a member select from the group consisting of phenyl, substituted phenyl, and pyridinyl, said substituted phenyl having from 1 to 2 independently-selected halo substituents.

9. A pharmaceutical composition according to claim 8 wherein Q is diarylmethyl and Alk is a 1,3-propanediyl radical.

10. A pharmaceutical composition according to claim 8 wherein Q is diarylmethyl and Alk is 1,3-propanediyl, X is aminocarbonyl, m is 1 and $R^2$ is both hydrogen.

11. A pharmaceutical composition according to claim 8 wherein Q is diarylmethyl, aryl is phenyl or substituted phenyl, X is aminocarbonyl, and $R^2$ is hydrogen.

12. A pharmaceutical composition in dosage unit form comprising per dosage unit an amount, effective in ameliorating the blood perfusion of the muscular tissues of the heart and/or effective in protecting, partially or completely, the heart from myocardial injury caused by more or less brief episodes of ischaemia, anoxia or hypoxia, of a compound selected from the group consisting of 3-(aminocarbonyl)-4-[4,4-bis(4-fluorophenyl)butyl]-N(2,6-dichlorophenyl)-1-piperazineacetamide, the stereochemically isomeric forms and the pharmaceutically acceptable acid addition salts thereof.

13. A method for ameliorating the blood perfusion of the muscular tissues of the heart and/or protecting, partially or completely, the heart from myocardial injury caused by more or less brief episodes of ischaemia, anoxia or hypoxia, of a compound having the formula the stereochemically isomeric forms and the pharmaceutically acceptable acid addition salts thereof, wherein $R^1$ is a member selected from the group consisting of hydrogen and lower alkyl;

X is a member selected from the group consisting of hydroxylower alkyl, lower alkyloxylower alkyl, aminocarbonyl, mono- and di(lower alkyl)aminocarbonyl, carboxyl, lower alkyloxycarbonyl, (aminocarbonyl)lower alkyl, [mono- and di(-lower alkyl)aminocarbonyl]lower alkyl, carboxylower alkyl, (lower alkyloxycarbonyl)lower alkyl and (hydroxylower alkyl)aminocarbonyl;

m is the integer 1 or 2;

$R^2$ is a member selected from the group consisting of hydrogen and lower alkyl;

$R^3$, $R^4$ and $R^5$ are each independently selected from the group consisting of hydrogen, hydroxy, lower alkyl, lower alkyloxy, halo, trifluoromethyl, lower alkylcarbonyl, aminocarbonyl, lower alkyloxycarbonyl, mono- and di(lower alkyl)amino, amino and (aminocarbonyl)amino, while $R^3$ may also be nitro cyano or amino; and R is a member selected from the group consisting of a radical a radical having the formula -Alk-Q  (b)

wherein

Alk is an alkanediyl or a lower alkenediyl radical, said lower alkanediyl radical being optionally substituted by a hydroxy- or a lower alkyl radical; and Q is a member selected from the group consisting of aryl, aryloxy, diarylmethoxy, 2,2-diarylethenyl, diarylmethylcarbonyl, mono- and diarylaminocarbonyl, diarylmethyl, the methyl moiety in said diarylmethyl group being optionally substituted with a cyano-, or a lower alkyloxycarbonyl radical, arylamino, said amino moiety being optionally substituted with an aryl-, radical, 2,3-dihydro-2-oxo-1H-benzimidazol-1-yl, being optionally substituted in the 5- or 6-position by halo, and 1-aryl-1,3-dihydroisobenzofuran-1-yl, wherein aryl is a member selected from the group consisting of phenyl, substituted phenyl, naphthalenyl, thienyl and pyridinyl, said substituted phenyl having from 1 to 2 substituents, each independently selected from the group consisting of halo and (halo-substituted phenyl)carbonyl.

14. A method for ameliorating the blood perfusion of the muscular tissues of the heart and/or protecting, partially or completely, the heart from myocardial injury caused by more or less brief episodes of ischaemia, anoxia or hypoxia, of a compound having the formula

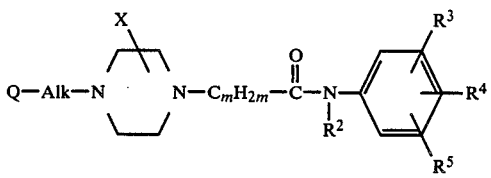

the stereochemically isomeric forms and the pharmaceutically acceptable acid addition salts thereof, wherein $R^2$ is a member selected from the group consisting of hydrogen and lower alkyl;

X is a member selected from the group consisting of hydroxyloweralkyl, aminocarbonyl, and (lower alkyl)aminocarbonyl;

m is the integer 1 or 2;

$R^3$, $R^4$ and $R^4$ are each independently selected from the group consisting of hydrogen, hydroxy, lower alkyl, lower alkyloxy, halo, trifluoromethyl, lower alkylcarbonyl, aminocarbonyl, lower alkyloxycarbonyl, mono- and di(lower alkyl)amino, and (aminocarbonyl)amino, while $R^3$ and/or $R^4$ may also be nitro, cyano or amino and Alk is an alkanediyl or a lower alkanediyl radical, said lower alkanediyl radical being optionally substituted by a hydroxy- or a lower alkyl radical; and Q is a member selected from the group consisting of aryl; diarylmethyl, the methyl moiety in said diarylmethyl group being optionally substituted with a cyano or a lower alkyloxycarbonyl radical; diarylamino; and 1-aryl-1,3-dihydroisobenzofuran-1-yl;

wherein aryl is a member selected from the group consisting of phenyl, substituted phenyl, and pyridinyl, said substituted phenyl having from 1 to 2 independently-selected halo substituents.

15. A method according to claim 14 wherein Q is diarylmethyl and Alk is a 1,3-propanediyl radical.

16. A method according to claim 14 wherein Q is diarylmethyl and Alk is 1,3-propanediyl, X is aminocarbonyl, m is 1 and $R^2$ is both hydrogen.

17. A method according to claim 14 wherein Q is diarylmethyl, aryl is phenyl or substituted phenyl, X is aminocarbonyl, and $R^2$ is hydrogen.

18. A method for ameliorating the blood perfusion of the muscular tissues of the heart and/or protecting, partially or completely, the heart from myocardial injury caused by more or less brief episodes of ischaemia, anoxia or hypoxia, of a compound selected from the group consisting of 3-(aminocarbonyl)-4-[4,4-bis(4-fluorophenyl)butyl]-N-(2,6-dichlorophenyl)-1-piperazineacetamide, the stereochemically isomeric forms and the pharmaceutically acceptable acid addition salts thereof.

* * * * *

UNITED STATES PATENT AND TRADEMARK OFFICE
CERTIFICATE OF CORRECTION

PATENT NO.   : 4,766,125
DATED        : August 23, 1988
INVENTOR(S)  : Georges Van Daele It is certified that error appears in the above-identified patent and that said Letters Patent is hereby corrected as shown below:

Claim 4, column 59, line 49, delete "$R^2$ is".

Claim 4, column 59, line 50, after and insert --$R^2$ is--.

Claim 10, column 61, line 48, delete "both".

Claim 16, column 64, line 15, delete "both".

Signed and Sealed this

Fourth Day of April, 1989

Attest:

DONALD J. QUIGG

Attesting Officer

Commissioner of Patents and Trademarks